(12) United States Patent
St. John et al.

(10) Patent No.: US 9,975,885 B2
(45) Date of Patent: May 22, 2018

(54) BROAD-SPECTRUM NON-COVALENT CORONAVIRUS PROTEASE INHIBITORS

(71) Applicant: Purdue Research Foundation, West Lafayette, IN (US)

(72) Inventors: Sarah Emma St. John, West Lafayette, IN (US); Andrew D. Mesecar, West Lafayette, IN (US)

(73) Assignee: PURDUE RESEARCH FOUNDATION, West Lafayette, IN (US)

( * ) Notice: Subject to any disclaimer, the term of this patent is extended or adjusted under 35 U.S.C. 154(b) by 0 days. days.

(21) Appl. No.: 15/581,122

(22) Filed: Apr. 28, 2017

(65) Prior Publication Data
US 2017/0313685 A1    Nov. 2, 2017

Related U.S. Application Data

(60) Provisional application No. 62/328,797, filed on Apr. 28, 2016.

(51) Int. Cl.
| | |
|---|---|
| *C07D 409/14* | (2006.01) |
| *C07D 209/20* | (2006.01) |
| *C07D 211/62* | (2006.01) |
| *C07D 233/64* | (2006.01) |
| *C07D 235/08* | (2006.01) |
| *C07D 249/18* | (2006.01) |
| *C07D 307/81* | (2006.01) |
| *C07D 401/12* | (2006.01) |
| *C07D 409/12* | (2006.01) |

(52) U.S. Cl.
CPC ........ *C07D 409/14* (2013.01); *C07D 209/20* (2013.01); *C07D 211/62* (2013.01); *C07D 233/64* (2013.01); *C07D 235/08* (2013.01); *C07D 249/18* (2013.01); *C07D 307/81* (2013.01); *C07D 401/12* (2013.01); *C07D 409/12* (2013.01)

(58) Field of Classification Search
CPC .. C07D 409/14; C07D 209/20; C07D 211/62; C07D 233/64; C07D 235/08; C07D 249/18; C07D 307/81; C07D 401/12; C07D 409/12
USPC ........................................................ 514/326
See application file for complete search history.

(56) References Cited

U.S. PATENT DOCUMENTS

| | | | |
|---|---|---|---|
| 2013/0184222 A1* | 7/2013 | Popovici-Muller ... | C07C 237/22 514/19.3 |
| 2016/0297751 A1* | 10/2016 | Kim ...................... | C07C 237/22 |

FOREIGN PATENT DOCUMENTS

| | | | |
|---|---|---|---|
| CN | 101875644 | * | 11/2010 |
| WO | WO2015037892 | * | 3/2015 |

OTHER PUBLICATIONS

Zuo; J. Agric. Food Chem. 2010, 58, 2755-2762. (Year: 2010).*
Marcaccini; Nature Protocols, 2007, 2, 632-639. (Year: 2007).*
Domling; Angew. Chem. Int. Ed. 2000, 39, 3168-3210. (Year: 2000).*

(Continued)

*Primary Examiner* — Daniel R Carcanague
(74) *Attorney, Agent, or Firm* — Purdue Research Foundation; Liang Zeng Yan

(57) ABSTRACT

This invention pertains to materials and methods for the treatment of patients with coronavirus infection and the control of zoonotic disease outbreaks using broad-spectrum non-covalent coronavirus protease inhibitors.

18 Claims, 12 Drawing Sheets

(56) References Cited

OTHER PUBLICATIONS

Lee; Anal. Biochem. 423 (2012) 46-53. (Year: 2012).*
Chemical Abstracts STN Registry Database record for RN 1033047-39-0, entered into the database on Jul. 8, 2008. 1 page. (Year: 2008).*
Turlington, M., "Discovery of N-(benzo[1,2,3]triazol-1-yl)-N-(benzyl)acetamido) phenyl) carboxamides as severe acute respiratory syndrome coronavirus (SARS-CoV) 3CLpro inhibitors." Bioorg. Med. Chem. Lett 23 (2013) 6172-6177.
Jacobs, J., "Discovery, Synthesis, and Structure-based Optimization of . . . " J. Med. Chem. 2013, 56, 534-546.
St. John, S., "Targeting zoonotic viruses: Structure-based inhibition of the 3C-like protease from bat coronavirus HKU4." Bioorganic & Medicinal Chemistry 23 (2015) 6036-6048.
Ghosh, A.K., "Design and Synthesis of Peptidomimetic Severe Acute Respiratory Syndrome Chymotrypsin-like Protease Inhibitors." Journal of Medicinal Chemistry, 2005, vol. 48, 6767-6771.
Anand, K., "Coronavirus Main Proteinase Structure." Science, vol. 300, No. 5626 (Jun. 13, 2003), pp. 1763-1767.
Woo, P. "Coronavirus Diversity, Phylogeny and Interspecies Jumping." Exp Biol Med 2009, 234:1117-1127.
Godfrey, A.G., "A remote-controlled adaptive medchem lab: an innovative approach to enable drug discovery in the 21st Century." Drug Discovery Today 2013, 18(17/18), 795-.
Perlman, S., "Coronaviruses post-SARS: update on replication and pathogenesis." Nature Reviews, Microbiology, 2009, 7, 439-450.

* cited by examiner

|       | IBV   |       |       |       |       |       |       |       |       |     |
|-------|-------|-------|-------|-------|-------|-------|-------|-------|-------|-----|
| IBV   | 100   | FIPV  |       |       |       |       |       |       |       |     |
| FIPV  | 42.33 | 100   | PEDV  |       |       |       |       |       |       |     |
| PEDV  | 42.33 | 61.92 | 100   | NL63  |       |       |       |       |       |     |
| NL63  | 39.33 | 57.95 | 69.21 | 100   | SARS  |       |       |       |       |     |
| SARS  | 40.67 | 44.37 | 45.36 | 43.38 | 100   | HKU9  |       |       |       |     |
| HKU9  | 38.33 | 41.72 | 45.36 | 42.72 | 51.96 | 100   | HKU4  |       |       |     |
| HKU4  | 40.53 | 49.34 | 47.68 | 48.68 | 51.16 | 52.15 | 100   | HKU5  |       |     |
| HKU5  | 38.20 | 48.01 | 48.01 | 48.68 | 50.83 | 51.82 | 83.66 | 100   | HKU1  |     |
| HKU1  | 42.00 | 46.03 | 44.70 | 43.38 | 48.51 | 48.18 | 52.15 | 52.81 | 100   | OC43 |
| OC43  | 41.00 | 44.37 | 43.05 | 42.38 | 47.19 | 47.52 | 50.83 | 51.16 | 81.52 | 100 |

Fig. 1B

| Cmpd. | OC43-3CL$^{pro}$ IC$_{50}$ (µM) | SARS-3CL$^{pro}$ IC$_{50}$ (µM) | HKU4-3CL$^{pro}$ IC$_{50}$ (µM) | HKU5-3CL$^{pro}$ IC$_{50}$ (µM) |
|---|---|---|---|---|
| 1P | 6.9 ± 0.9 | 1.6 ± 0.2 | 1.1 ± 0.1 | 1.2 ± 0.1 |
| 2P | 24.4 ± 3.5 | 8.9 ± 1.4 | 3.8 ± 0.3 | 3.5 ± 0.5 |
| 3P | 13.7 ± 1.5 | 6.2 ± 0.4 | 7.0 ± 0.5 | 6.2 ± 0.8 |

BROAD-SPECTRUM NON-COVALENT CORONAVIRUS PROTEASE INHIBITORS

CROSS-REFERENCE TO RELATED APPLICATIONS

The present U.S. patent application is related to and claims the priority benefit of U.S. Provisional Patent Application Ser. No. 62/328,797, filed Apr. 28, 2016, the contents of which are hereby incorporated by reference in their entirety into the present disclosure.

GOVERNMENT SUPPORT

This invention was made with government support under AI026603 and AI085089, awarded by the Institutes of Health. The government has certain rights in the invention.

TECHNICAL FIELD

The present disclosure generally relates to materials and methods useful for the treatment of patients with coronavirus infection and the control of zoonotic viral disease outbreaks, and in particular to broad-spectrum non-covalent anti-coronavirus therapeutics.

BACKGROUNDS

This section introduces aspects that may help facilitate a better understanding of the disclosure. Accordingly, these statements are to be read in this light and are not to be understood as admissions about what is or is not prior art.

The Coronaviridae family of viruses are enveloped, single-stranded, positive-sense RNA viruses and include 141 species that are classified into four genera according to their phylogenetic relationships: α-, β-, γ-, and δ-coronavirus (FIGS. 1A-1B) (Woo, et al., *Exp. Biol. Med.* 2009, 234(10): 1117-1127). Coronaviruses (CoVs) are zoonotic viruses that infect a variety of animals from whales to birds, bats, cats, and humans. Typically, CoV infection results in mild to moderate respiratory tract infections; however, some CoV species are extremely virulent and can result in widespread fatality. Severe acute respiratory syndrome coronavirus (SARS-CoV) is a human CoV that was responsible for the first pandemic of the 21$^{st}$ century, infecting over 8,000 people with a 10% mortality rate (Perlman, S., et al., *Nature Reviews Microbiology* 2009, 7(6):439-450). More recently, Middle East respiratory syndrome coronavirus (MERS-CoV) was identified in November 2012 and had since infected over 1,600 people in 26 countries with 36% mortality rate (Chan, et al., *J. Formos. Med. Assoc.* 2013, 112(7): 372-381).

These especially virulent CoV species arise from inter-species jumping, or zoonotic shifts, which have led to particularly disastrous outbreaks of zoonotic disease. SARS-CoV originated from the Guangdong Province of China in November 2002, where the origin of transmission to humans was identified to be palm civets butchered for food and purchased at exotic animal markets (Xu, et al., *Emerg. Infect. Dis.* 2004, 10(6):1030-1037; Guan, et al., *Science,* 2003, 302(5643): 276-278). Horseshoe bats were subsequently identified as the zoonotic reservoir of SARS-CoV (Lau, et al., *Proc Natl Acad Sci USA* 2005, 102(39):14040-14045). MERS-CoV is also believed to originate from a bat reservoir as it is genetically related to the bat coronaviruses HKU4 and HKU5, and utilizes the same cellular receptor as HKU4 (Yang, et al., *Proc Natl Acad Sci USA* 2014, 111(34): 12516-12521). The origin of MERS-CoV transmission from bats to humans is likely facilitated by dromedary camels as the intermediary host (Reusken, C. B., et al., *The Lancet Infectious diseases* 2013, 13(10):859-866).

All CoVs express a >800 kDa replicase polyprotein that contains either two or three cysteine proteases, the papain-like protease(s) (PLP$^{pro}$, or PLP1 and PLP2) and the 3C-like protease (3CL$^{pro}$, nsp5, or M$^{pro}$). These proteases process the CoV replicase polyprotein by cleaving it into 16 non-structural proteins, which are responsible for a variety of aspects of CoV replication (Perlman, S et al., *Nature Rev. Microbiol.* 2009, 7(6): 439-450). The CoV 3CL$^{pro}$ is responsible for processing 11 cleavage sites of within the replicase polyprotein and is essential for CoV replication, making it a highly valuable target for therapeutic development (Ghosh, et al., *J Med Chem* 2005, 48(22):6767-6771). Furthermore, the overall active site architecture and substrate recognition pockets are structurally conserved across CoV 3CL$^{pro}$'s, increasing its attractiveness as a target for the development of broad-spectrum anti-CoV therapeutics.

Previous efforts at the design and development of broad-spectrum CoV 3CL$^{pro}$ inhibitors have focused on substrate-mimetic peptidyl inhibitors containing electrophilic warheads capable of covalently reacting with and modifying the 3CL$^{pro}$ catalytic cysteine (Anand, et al., *Science* 2003, 300(5626): 1763-1767; Kim, et al., *J. Virology* 2015, 89(9): 4942-4950). However, though this class of 3CL$^{pro}$ inhibitors has been known for over a decade, an effective commercially available broad-spectrum therapeutic has yet to be developed. There is a critical need for the development of broad-spectrum CoV therapeutics to overcome the challenges of traditional anti-CoV therapeutic development, as broad-spectrum therapeutics can be rapidly implemented upon zoonotic disease outbreak.

BRIEF SUMMARY OF INVENTION

In some embodiments, this invention pertains to a compound of formula (I)

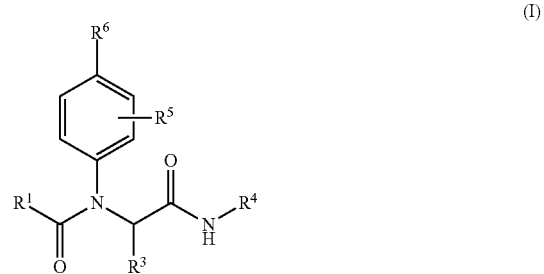

or a pharmaceutically acceptable salt or hydrate thereof, wherein:

$R^1$ is 1H-imidazole-4-yl; 1H-benzo[d][1,2,3]triazol-1-yl methyl, 1H-benzo[d]imidazol-1-yl methyl, 1H-benzo[d]imidazol-2-yl ethyl, 7-methyl-1H-indol-3-yl methyl, benofuran-3-yl methyl, tert-butyl piperidine-1-carboxylate-4-yl, or 2-methyl-1H-imidazol-1-yl ethyl;

$R^3$ is an optionally substituted $C_3$-$C_{12}$ alkyl, alkenyl, cycloalkyl, cycloalkenyl, heterocycle (heterocyclic), aryl, or heteroaryl;

$R^4$ is an optionally substituted $C_3$-$C_{12}$ alkyl, alkenyl, cycloalkyl, cycloalkenyl, heterocycle (heterocyclic), aryl, or heteroaryl;

R⁵ represents 1~4 substituents each of which is independently selected from the group comprising of hydrogen, halo, or an optionally substituted $C_1$~$C_{12}$ alkyl, alkoxy, acyl, alkyl amide, cycloalkyl, cycloalkenyl, cycloalkyl amide, or aryl; or R⁵ represents 2-4 substituents where 2 adjacent substituents are taken together with the attached carbons to form an optionally substituted cyclic or heterocyclic moiety, and where any remaining substituents are each independently selected from the group as defined above; and R⁶ is halo or an optionally substituted $C_1$~$C_{12}$ alkyl amide, cycloalkyl amide, alkyl, alkenyl, alkoxy, acyl, cycloalkyl, cycloalkenyl, heterocycle (heterocyclic), aryl, or heteroaryl.

In some embodiments, this invention pertains to a pharmaceutical composition comprising a compound disclosed herein, or a pharmaceutically acceptable salt thereof, together with one or more pharmaceutically acceptable carriers, diluents, and excipients.

In some embodiments, this invention pertains to a compound having the following pharmaceutical composition comprising a compound disclosed herein, in combination with one or more other therapeutically active compounds by the same or different mode of action, and one or more pharmaceutically acceptable carriers, diluents, and excipients.

In some embodiments, this invention pertains to a method for treating a patient of viral infection, the method comprising the step of administering a therapeutically effective amount of a compound disclosed herein, together with one or more pharmaceutically acceptable carriers, diluents, and excipients, to the patient in need of relief from said viral infection.

In some embodiments, this invention pertains to a method for treating a patient of viral infection, the method comprising the step of administering a therapeutically effective amount of a compound disclosed herein, in combination with one or more therapeutically effective compounds by the same or different mode of action, to the patient in need of relief from said viral infection.

In some other embodiments, this invention pertains to a method for treating a patient of viral infection, the method comprising the step of administering a therapeutically effective amount of a compound of formula (I):

(I)

[chemical structure]

or a pharmaceutically acceptable salt or hydrate thereof, wherein:

R¹ is 1H-imidazole-4-yl; 1H-benzo[d][1,2,3]triazol-1-yl methyl, 1H-benzo[d]imidazol-1-yl methyl, 1H-benzo[d]imidazol-2-yl ethyl, 7-methyl-1H-indol-3-yl methyl, benofuran-3-yl methyl, tert-butyl piperidine-1-carboxylate-4-yl, or 2-methyl-1H-imidazol-1-yl ethyl;

R³ is an optionally substituted $C_3$~$C_{12}$ alkyl, alkenyl, cycloalkyl, cycloalkenyl, heterocycle (heterocyclic), aryl, or heteroaryl;

R⁴ is an optionally substituted $C_3$~$C_{12}$ alkyl, alkenyl, cycloalkyl, cycloalkenyl, heterocycle (heterocyclic), aryl, or heteroaryl;

R⁵ represents 1~4 substituents each of which is independently selected from the group comprising of hydrogen, halo, or an optionally substituted $C_1$~$C_{12}$ alkyl, alkoxy, acyl, alkyl amide, cycloalkyl, cycloalkenyl, cycloalkyl amide, or aryl; or R⁵ represents 2-4 substituents where 2 adjacent substituents are taken together with the attached carbons to form an optionally substituted cyclic or heterocyclic moiety, and where any remaining substituents are each independently selected from the group as defined above; and R⁶ is halo or an optionally substituted $C_1$~$C_{12}$ alkyl amide, cycloalkyl amide, alkyl, alkenyl, alkoxy, acyl, cycloalkyl, cycloalkenyl, heterocycle (heterocyclic), aryl, or heteroaryl.

It is appreciated herein that the compounds described herein may be used alone or in combination with other compounds that may be therapeutically effective by the same or different modes of action. In addition, it is appreciated herein that the compounds described herein may be used in combination with other compounds that are administered to treat other symptoms of viral infections, such as compounds administered to relieve pain, nausea, vomiting, and the like.

BRIEF DESCRIPTION OF THE FIGURES

FIG. 1B shows the percent identity matrix of the coronaviral 3CL$^{pro}$'s, from different phylogenetic groups and subgroups, all of which were tested for inhibition by the broad-spectrum library.

DETAILED DESCRIPTION

Figure 1A:
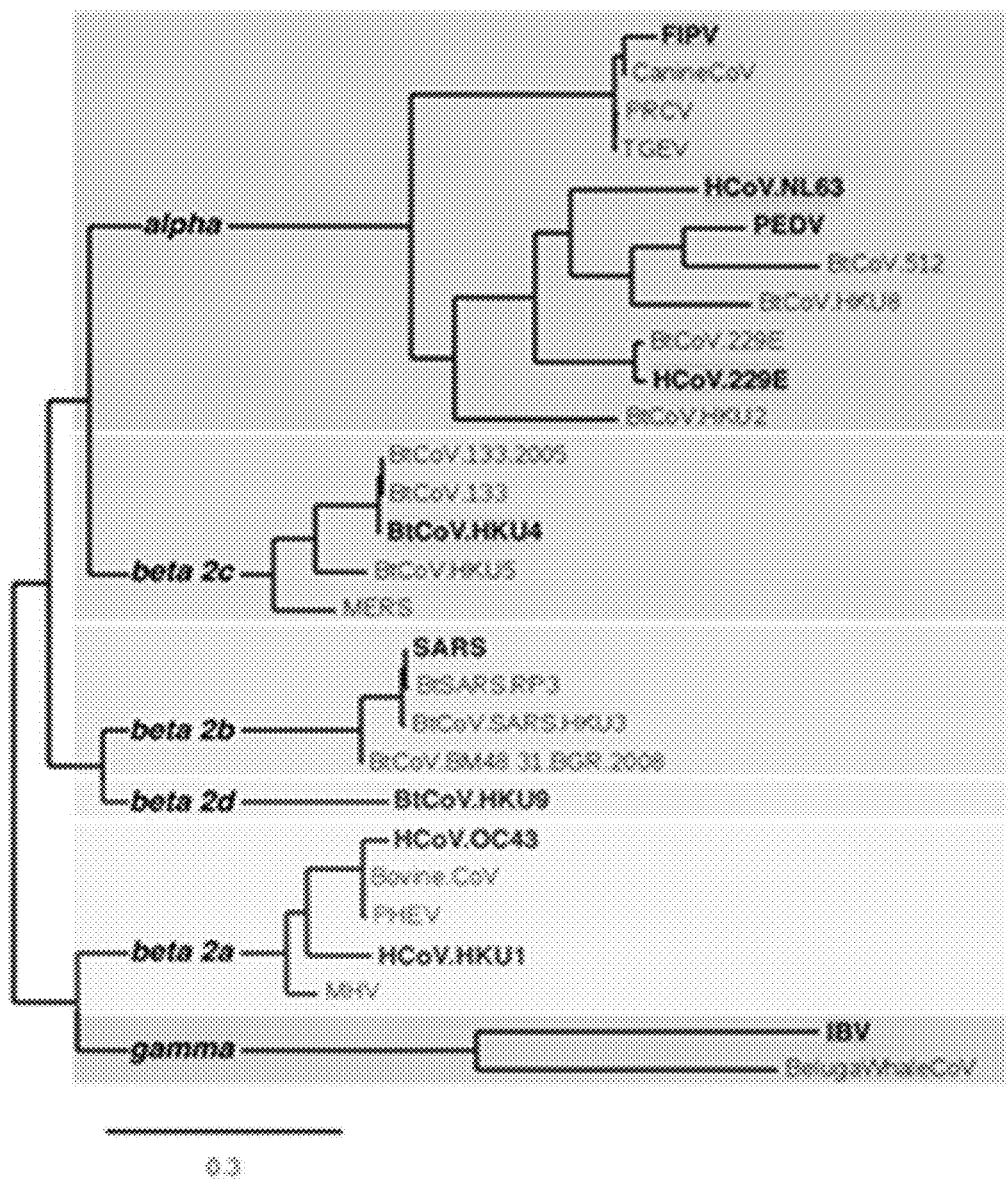
FIG. 1A is a schematic phylogenetic tree (phylogram) of full 3CL$^{pro}$ sequences of 28 coronaviruses, which were aligned and phylogenetically compared. Three distinct phylogenetic groups are displayed: alpha- (purple), beta- (gradient indigo), and gammacoronaviruses (grey). The subgroup clusters (2a-2d) are displayed for the betacoronaviruses. The phylogram was generated using MUSCLE for multiple alignment and PhyML for phylogeny within the website of www.phylogeny.fr.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

As used herein, the following terms and phrases shall have the meanings set forth below. Unless defined otherwise, all technical and scientific terms used herein have the same meaning as commonly understood to one of ordinary skill in the art.

In the present disclosure the term "about" can allow for a degree of variability in a value or range, for example, within 10%, within 5%, or within 1% of a stated value or of a stated limit of a range. In the present disclosure the term "substantially" can allow for a degree of variability in a value or range, for example, within 90%, within 95%, 99%, 99.5%, 99.9%, 99.99%, or at least about 99.999% or more of a stated value or of a stated limit of a range.

A "halogen" designates F, Cl, Br or I. A "halogen-substitution" or "halo" substitution designates replacement of one or more hydrogen atoms with F, Cl, Br or I.

As used herein, the term "alkyl" refers to a saturated monovalent chain of carbon atoms, which may be optionally branched. It is understood that in embodiments that include alkyl, illustrative variations of those embodiments include lower alkyl, such as $C_1$-$C_6$ alkyl, methyl, ethyl, propyl, 3-methylpentyl, and the like.

As used herein, the term "alkenyl" refers to an unsaturated monovalent chain of carbon atoms including at least one double bond, which may be optionally branched. It is understood that in embodiments that include alkenyl, illustrative variations of those embodiments include lower alkenyl, such as $C_2$-$C_6$, $C_2$-$C_4$ alkenyl, and the like.

As used herein, the term "alkynyl" refers to an unsaturated monovalent chain of carbon atoms including at least one triple bond, which may be optionally branched. It is understood that in embodiments that include alkynyl, illustrative variations of those embodiments include lower alkynyl, such as $C_2$-$C_6$, $C_2$-$C_4$ alkynyl, and the like.

As used herein, the term "cycloalkyl" refers to a monovalent chain of carbon atoms, a portion of which forms a ring. It is understood that in embodiments that include cycloalkyl, illustrative variations of those embodiments include lower cylcoalkyl, such as $C_3$-$C_8$ cycloalkyl, cyclopropyl, cyclohexyl, 3-ethylcyclopentyl, and the like.

As used herein, the term "cycloalkenyl" refers to an unsaturated monovalent chain of carbon atoms, a portion of which forms a ring. It is understood that in embodiments that include cycloalkenyl, illustrative variations of those embodiments include lower cycloalkenyl, such as $C_3$-$C_8$, $C_3$-$C_6$ cycloalkenyl.

As used herein, the term "alkylene" refers to a saturated bivalent chain of carbon atoms, which may be optionally branched. It is understood that in embodiments that include alkylene, illustrative variations of those embodiments include lower alkylene, such as C2-C4, alkylene, methylene, ethylene, propylene, 3-methylpentylene, and the like.

As used herein, the term "heterocyclic" or "heterocycle" refers to a monovalent chain of carbon and heteroatoms, wherein the heteroatoms are selected from nitrogen, oxygen, and sulfur, and a portion of which, at least one heteroatom, forms a ring. The term "heterocycle" may include both "aromatic heterocycles" and "non-aromatic heterocycles." Heterocycles include 4-7 membered monocyclic and 8-12 membered bicyclic rings, such as imidazolyl, thiazolyl, oxazolyl, oxazinyl, thiazinyl, dithianyl, dioxanyl, isoxazolyl, isothiazolyl, triazolyl, furanyl, tetrahydrofuranyl, dihydrofuranyl, pyranyl, tetrazolyl, pyrazolyl, pyrazinyl, pyridazinyl, imidazolyl, pyridinyl, pyrrolyl, dihydropyrrolyl, pyrrolidinyl, piperidinyl, piperazinyl, pyrimidinyl, morpholinyl, tetrahydrothiophenyl, thiophenyl, azetidinyl, oxetanyl, thiiranyl, oxiranyl, aziridinyl, and the like. "Heterocycles" may be optionally substituted at any one or more positions capable of bearing a hydrogen atom.

As used herein, the term "aryl" includes monocyclic and polycyclic aromatic carbocyclic groups, each of which may be optionally substituted. The term "optionally substituted aryl" refers to an aromatic mono or polycyclic ring of carbon atoms, such as phenyl, naphthyl, and the like, which may be optionally substituted with one or more independently selected substituents, such as halo, hydroxyl, amino, alkyl, or alkoxy, alkylsulfony, cyano, nitro, and the like.

The term "heteroaryl" or "aromatic heterocycle" includes substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The term "heteroaryl" may also include ring systems having one or two rings wherein at least one of the rings is heteroaromatic, e.g., the other cyclic rings can be cycloalkyl, cycloalkenyl, cycloalkynyl, aromatic carbocycle, heteroaryl, and/or heterocycle. Heteroaryl groups include, for example, pyrrole, furan, thiophene, imidazole, oxazole, thiazole, pyrazole, pyridine, pyrazine, pyridazine, and pyrimidine.

It is understood that each of alkyl, cycloalkyl, alkenyl, cycloalkenyl, alkylene, and heterocycle may be optionally substituted with independently selected groups such as alkyl, haloalkyl, hydroxyalkyl, aminoalkyl, carboxylic acid and derivatives thereof, including esters, amides, and nitrites, hydroxy, alkoxy, acyloxy, amino, alky and dialkylamino, acylamino, thio, and the like, and combinations thereof.

The term "optionally substituted," or "optional substituents," as used herein, means that the groups in question are either unsubstituted or substituted with one or more of the substituents specified. When the groups in question are substituted with more than one substituent, the substituents may be the same or different. Furthermore, when using the terms "independently," "independently are," and "independently selected from" mean that the groups in question may be the same or different. Certain of the herein defined terms may occur more than once in the structure, and upon such occurrence each term shall be defined independently of the other.

The term "patient" includes human and non-human animals such as companion animals (dogs and cats and the like) and livestock animals. Livestock animals are animals raised for food production. The patient to be treated is preferably a mammal, in particular a human being.

The term "pharmaceutically acceptable carrier" is art-recognized and refers to a pharmaceutically-acceptable material, composition or vehicle, such as a liquid or solid filler, diluent, excipient, solvent or encapsulating material, involved in carrying or transporting any subject composition or component thereof. Each carrier must be "acceptable" in the sense of being compatible with the subject composition and its components and not injurious to the patient. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

As used herein, the term "administering" includes all means of introducing the compounds and compositions described herein to the patient, including, but are not limited to, oral (po), intravenous (iv), intramuscular (im), subcutaneous (sc), transdermal, inhalation, buccal, ocular, sublingual, vaginal, rectal, and the like. The compounds and compositions described herein may be administered in unit dosage forms and/or formulations containing conventional nontoxic pharmaceutically acceptable carriers, adjuvants, and vehicles.

As used herein, the term "therapeutically effective amount" refers to that amount of active compound or pharmaceutical agent that elicits the biological or medicinal response in a tissue system, animal or human that is being sought by a researcher, veterinarian, medical doctor or other clinicians, which includes alleviation of the symptoms of the disease or disorder being treated. In one aspect, the therapeutically effective amount is that which may treat or alleviate the disease or symptoms of the disease at a reasonable benefit/risk ratio applicable to any medical treatment.

However, it is to be understood that the total daily usage of the compounds and compositions described herein may be decided by the attending physician within the scope of sound medical judgment. The specific therapeutically effective dose level for any particular patient will depend upon a variety of factors, including the disorder being treated and the severity of the disorder; activity of the specific compound employed; the specific composition employed; the age, body weight, general health, gender, and diet of the patient: the time of administration, and rate of excretion of the specific compound employed, the duration of the treatment, the drugs used in combination or coincidentally with the specific compound employed; and like factors well known to the researcher, veterinarian, medical doctor or other clinician of ordinary skill.

Depending upon the route of administration, a wide range of permissible dosages are contemplated herein, including doses falling in the range from about 1 µg/kg to about 1 g/kg. The dosage may be single or divided, and may administered according to a wide variety of dosing protocols, including q.d. (once per day), b.i.d. (twice per day), t.i.d. (three times per day), or even every other day, once a week, once a month, and the like. In each case the therapeutically effective amount described herein corresponds to the instance of administration, or alternatively to the total daily, weekly, or monthly dose, and the like.

In some embodiments, this invention pertains to a compound of formula (I)

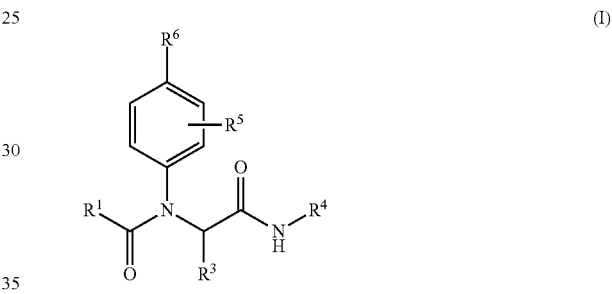

or a pharmaceutically acceptable salt or hydrate thereof, wherein:

$R^1$ is 1H-imidazole-4-yl; 1H-benzo[d][1,2,3]triazol-1-yl methyl, 1H-benzo[d]imidazol-1-yl methyl, 1H-benzo[d]imidazol-2-yl ethyl, 7-methyl-1H-indol-3-yl methyl, benofuran-3-yl methyl, tert-butyl piperidine-1-carboxylate-4-yl, or 2-methyl-1H-imidazol-1-yl ethyl;

$R^3$ is an optionally substituted $C_3$~$C_{12}$ alkyl, alkenyl, cycloalkyl, cycloalkenyl, heterocycle (heterocyclic), aryl, or heteroaryl;

$R^4$ is an optionally substituted $C_3$~$C_{12}$ alkyl, alkenyl, cycloalkyl, cycloalkenyl, heterocycle (heterocyclic), aryl, or heteroaryl;

$R^5$ represents 1~4 substituents each of which is independently selected from the group comprising of hydrogen, halo, or an optionally substituted $C_1$~$C_{12}$ alkyl, alkoxy, acyl, alkyl amide, cycloalkyl, cycloalkenyl, cycloalkyl amide, or aryl; or $R^5$ represents 2-4 substituents where 2 adjacent substituents are taken together with the attached carbons to form an optionally substituted cyclic or heterocyclic moiety, and where any remaining substituents are each independently selected from the group as defined above; and $R^6$ is halo or an optionally substituted $C_1$~$C_{12}$ alkyl amide, cycloalkyl amide, alkyl, alkenyl, alkoxy, acyl, cycloalkyl, cycloalkenyl, heterocycle (heterocyclic), aryl, or heteroaryl.

In some embodiments, this invention pertains to a compound of formula (I), wherein $R^1$ is 1H-imidazole-4-yl; 1H-benzo[d][1,2,3]triazol-1-yl methyl, 1H-benzo[d]imidazol-1-yl methyl, 1H-benzo[d]imidazol-2-yl methyl, 7-methyl-1H-indol-3-yl methyl, benofuran-3-yl methyl, or 2-methyl-1H-imidazol-1-yl ethyl.

In some embodiments, this invention pertains to a compound of formula (I), wherein $R^1$ is 1H-imidazole-4-yl or 1H-benzo[d][1,2,3]triazol-1-yl methyl.

In some other embodiments, this invention pertains to a compound of formula (I), wherein $R^3$ is an optionally substituted aryl or heterocycle.

In some embodiments, this invention pertains to a compound of formula (I), wherein $R^3$ is thiophene-3-yl or 3'-pyridyl.

In some embodiments, this invention pertains to a compound of formula (I), wherein $R^4$ is an optionally substituted $C_4$-$C_{12}$ alkyl, cycloalkyl, or aryl.

In some embodiments, this invention pertains to a compound of formula (I), wherein $R^4$ is cyclohexyl, cyclopentyl, t-butyl, isobutyl, neopentyl, or benzyl.

In some embodiments, this invention pertains to a compound of formula (I), wherein $R^5$ is hydrogen.

In some embodiments, this invention pertains to a compound of formula (I), wherein $R^6$ is an optionally substituted $C_4$-$C_{12}$ alkyl, alkylamide, cycloalkyl, or cycloalkylamide.

In some embodiments, this invention pertains to a compound of formula (I), wherein $R^6$ is isobutyramide or t-butyl.

In some embodiments, this invention pertains to a compound of formula (I), wherein $R^5$ is hydrogen and $R^6$ is isobutyramide or t-butyl.

In some embodiments, this invention pertains to a compound of formula (I), wherein $R^3$ is 3'-pyridyl; $R^5$ is hydrogen; and $R^6$ is isobutyramide or t-butyl.

In some embodiments, this invention pertains to a compound of formula (I), wherein $R^3$ is 3'-pyridyl; $R^5$ is hydrogen; $R^6$ is t-butyl; and $R^4$ is selected from the group consisting of cyclohexyl, cyclopentyl, t-butyl, isobutyl, neopentyl, and benzyl.

In some embodiments, this invention pertains to a compound of formula (I), wherein $R^1$ is 1H-imidazole-4-yl; $R^3$ is 3'-pyridyl; $R^5$ is hydrogen; and $R^4$ is selected from the group consisting of cyclohexyl, cyclopentyl, t-butyl, isobutyl, neopentyl, and benzyl.

In some embodiments, this invention pertains to a compound of formula (I), wherein $R^1$ is 1H-imidazole-4-yl; $R^3$ is 3'-pyridyl; $R^5$ is hydrogen; $R^6$ is t-butyl; and $R^4$ is selected from the group consisting of cyclohexyl, cyclopentyl, t-butyl, isobutyl, neopentyl, and benzyl.

In some embodiments, this invention pertains to a compound of formula (I), wherein $R^1$ is 1H-imidazole-4-yl; $R^3$ is 3'-pyridyl; $R^5$ is hydrogen; $R^6$ is t-butyl; and $R^4$ is cyclopentyl.

In some embodiments, this invention pertains to a compound of formula (I), wherein $R^1$ is 1H-imidazole-4-yl; $R^3$ is 3'-pyridyl; $R^5$ is hydrogen; $R^6$ is t-butyl; and $R^4$ is cyclohexyl.

In some embodiments, this invention pertains to a compound of formula (I), wherein $R^1$ is 1H-benzo[d][1,2,3]triazol-1-yl methyl; $R^3$ is meta-fluoro phenyl; $R^4$ is 3'-pyridyl methyl; $R^5$ is hydrogen; and $R^6$ is isobutyramide.

In some embodiments, this invention pertains to a compound of formula (I), wherein $R^1$ is 1H-benzo[d][1,2,3]triazol-1-yl methyl; $R^3$ is thiophene-3-yl; $R^5$ is hydrogen; $R^6$ is cyclopropanylamide; and $R^4$ is selected from the group consisting of cyclohexyl, cyclopentyl, cyclopropyl, t-butyl, isobutyl, isopropyl, neopentyl, 3-pyridylmethyl, 2-(t-butoxy)-2-oxoethyl, and benzyl.

In some embodiments, this invention pertains to a compound of formula (I), wherein $R^1$ is 1H-benzo[d][1,2,3] triazol-1-yl methyl; $R^3$ is thiophene-3-yl; $R^5$ is hydrogen; $R^6$ is cyclopropanylamide; and $R^4$ is 2-(t-butoxy)-2-oxoethyl.

In some embodiments, this invention pertains to a compound having the following structure of

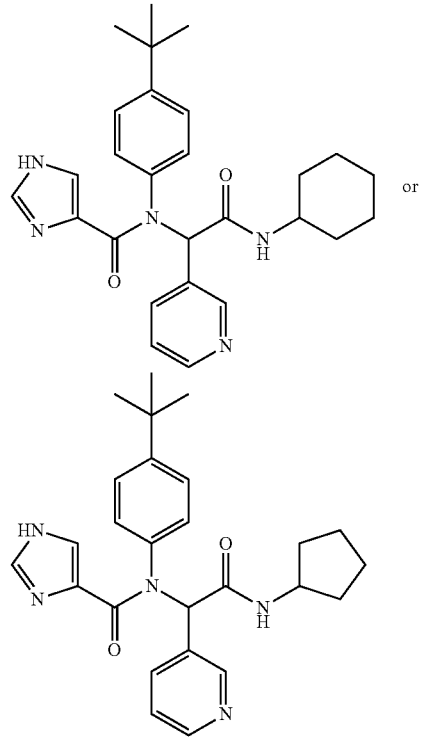

or a pharmaceutically acceptable salt or hydrate thereof.

In some embodiments, this invention pertains to a pharmaceutical composition comprising a compound disclosed herein, or a pharmaceutically acceptable salt thereof, together with one or more pharmaceutically acceptable carriers, diluents, and excipients.

In some embodiments, this invention pertains to pharmaceutical compositions containing one or more of the compounds are also described herein. In one aspect, the compositions include a therapeutically effective amount of the one or more compounds for treating a patient with viral infection. It is to be understood that the compositions may include other component and/or ingredients, including, but not limited to, other therapeutically active compounds with the same or different modes of action, and one or more carriers, diluents, excipients, and the like.

In some embodiments, this invention pertains to a method for treating a patient of viral infection, the method comprising the step of administering a therapeutically effective amount of a compound disclosed herein, together with one or more pharmaceutically acceptable carriers, diluents, and excipients, to the patient in need of relief from said viral infection.

In some embodiments, this invention pertains to a method for treating a patient of viral infection, the method comprising the step of administering a therapeutically effective amount of a compound disclosed herein, in combination with one or more therapeutically effective compounds by the same or different mode of action, to the patient in need of relief from said viral infection.

In some other embodiments, this invention pertains to a method for treating a patient of viral infection, the method comprising the step of administering a therapeutically effective amount of a compound of formula (I):

$$\text{(I)}$$

[Chemical structure of formula (I) showing a phenyl ring with R6 and R5 substituents connected to an NH-C(R3)-C(=O)-NH-R4 chain, with R1-C(=O)-N on the nitrogen]

or a pharmaceutically acceptable salt or hydrate thereof, wherein:

$R^1$ is 1H-imidazole-4-yl; 1H-benzo[d][1,2,3]triazol-1-yl methyl, 1H-benzo[d]imidazol-1-yl methyl, 1H-benzo[d]imidazol-2-yl ethyl, 7-methyl-1H-indol-3-yl methyl, benofuran-3-yl methyl, tert-butyl piperidine-1-carboxylate-4-yl, or 2-methyl-1H-imidazol-1-yl ethyl;

$R^3$ is an optionally substituted $C_3$~$C_{12}$ alkyl, alkenyl, cycloalkyl, cycloalkenyl, heterocycle (heterocyclic), aryl, or heteroaryl;

$R^4$ is an optionally substituted $C_3$~$C_{12}$ alkyl, alkenyl, cycloalkyl, cycloalkenyl, heterocycle (heterocyclic), aryl, or heteroaryl;

$R^5$ represents 1~4 substituents each of which is independently selected from the group comprising of hydrogen, halo, or an optionally substituted $C_1$~$C_{12}$ alkyl, alkoxy, acyl, alkyl amide, cycloalkyl, cycloalkenyl, cycloalkyl amide, or aryl; or $R^5$ represents 2-4 substituents where 2 adjacent substituents are taken together with the attached carbons to form an optionally substituted cyclic or heterocyclic moiety, and where any remaining substituents are each independently selected from the group as defined above; and $R^6$ is halo or an optionally substituted $C_1$~$C_{12}$ alkyl amide, cycloalkyl amide, alkyl, alkenyl, alkoxy, acyl, cycloalkyl, cycloalkenyl, heterocycle (heterocyclic), aryl, or heteroaryl.

It is appreciated herein that the compounds described herein may be used alone or in combination with other compounds that may be therapeutically effective by the same or different modes of action. In addition, it is appreciated herein that the compounds described herein may be used in combination with other compounds that are administered to treat other symptoms of viral infections, such as compounds administered to relieve pain, nausea, vomiting, and the like.

It is appreciated herein that the compounds described herein may be used alone or in combination with other compounds useful for treating viral infection, including those compounds that may be therapeutically effective by the same or different modes of action.

The following non-limiting exemplary embodiments are included herein to further illustrate the invention. These exemplary embodiments are not intended and should not be interpreted to limit the scope of the invention in any way. It is also to be understood that numerous variations of these exemplary embodiments are contemplated herein.

Figure 2A:
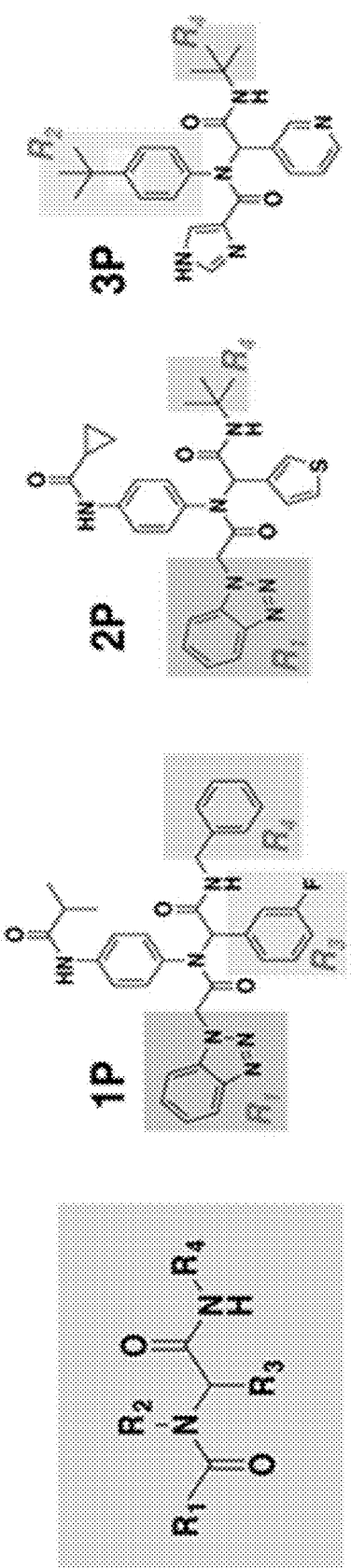
FIG. 2A shows the peptidomimetic backbone and chemical structures of previously reported three parent compounds 1P, 2P, and 3P.
Figures 2B, 2C:
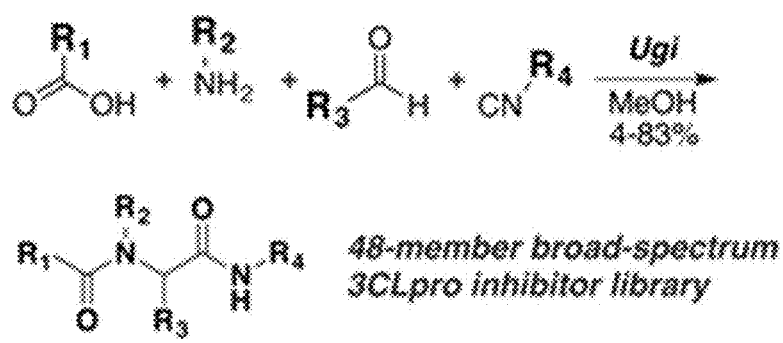
FIG. 2B demonstrates the inhibition of OC43-, SARS-, HKU4-, and HKU5-3CL$^{pro}$ by the three parent compounds.
FIG. 2C shows the design and synthesis of 48-member library, where the four R-groups are systematically varied on each of the parent scaffolds.

Design and Synthesis of Broad-Spectrum Coronaviral 3CL$^{pro}$ Inhibitor Library To assess the potential for non-covalent broad-spectrum CoV 3CL$^{pro}$ inhibition, a previously reported library of 205 peptidomimetics that were synthesized for the inhibition of SARS-3CL$^{pro}$ against the β-CoV OC43-, SARS-, HKU4-, and HKU5-3CL$^{pro}$'s identified three compounds, 1P, 2P, and 3P, which were capable of inhibiting all four of the beta-CoV 3CL$^{pro}$'s with IC$_{50}$ values ranging from 1.1 to 24.4 μM (FIGS. 2A-2B) (Jacobs, et al., *J. Med. Chem.* 2013, 56(2): 534-546; Turlington, et al., *Bioorg. Med. Chem. Lett.* 2013, 23(22):6172-6177). Because 1P, 2P, and 3P were the only compounds of the 205 tested capable of inhibiting multiple 3CL$^{pro}$'s from this first generation library, their scaffolds were used as templates for the design of a small second generation library of 48 peptidomimetic compounds for broad-spectrum non-covalent CoV 3CL$^{pro}$ inhibition. The $R_1$, $R_2$, $R_3$, and $R_4$ positions of 1P, 2P, and 3P were systematically varied to produce a library with different heterocycles and substituents at these positions to probe the steric, electronic, and hydrogen-bonding requirements for broad-spectrum non-covalent CoV 3CL$^{pro}$ inhibition (FIGS. 2A-2C).

The rapid synthesis of the 48-member broad-spectrum library was accomplished through a multi-component Ugi reaction (FIG. 2C) (Godfrey, et al., *Drug Discov Today* 2013, 18(17-18):795-802). The structures of the 48 library members and yields are summarized in Tables 1A-1C. The $R_1$, $R_3$, and $R_4$ positions of first-generation compound 1P were investigated by synthesizing six compounds with $R_1$ heterocycle substitutions (compounds 19-20, 56-59), ten compounds with $R_3$ phenyl substitutions (compounds 11-16, 51-52, 54-55), and one compound where the $R_4$ benzyl was replaced (compound 6). The $R_1$ and $R_4$ positions of 2P were chosen for further investigation by synthesizing eight compounds with $R_1$ heterocycle substitutions (compounds 24-27, 60-63) and nine compounds where the $R_4$ tert-butyl of 2P was varied (compounds 29-34, 37, 64, 67). Finally, the $R_2$ and $R_4$ positions of 3P were further investigated by synthesizing eight compounds with $R_2$ substitutions (compounds 38-42, 69-71) and six compounds with $R_4$ variations (compounds 43-44, 46-48, 77). In addition, compounds 1P, 2P, and 3P were resynthesized so they could be tested concomitant with the 48-member library for broad-spectrum CoV 3CL$^{pro}$ inhibition as shown in Tables 1A-1C below.

TABLE 1A

Designed Broad-Spectrum Coronaviral 3CL$^{pro}$ Inhibitors from 1P.

| Inhibitor | R-Group Substituted | R$_1$ | R$_3$ | R$_4$ | % Yield | Score | Gini Coefficient |
|---|---|---|---|---|---|---|---|
| 1P | N/A | benzotriazolyl-CH(CH₃)- | 3-F-phenyl | benzyl | 4 | 5.7 | 0.31 |
| 6 | R$_4$ | benzotriazolyl-CH(CH₃)- | 3-F-phenyl | (pyridin-3-yl)methyl | 5 | 4.0* | 0.22* |
| 11 | R$_3$ | benzotriazolyl-CH(CH₃)- | 3-Cl-phenyl | benzyl | 24 | | 0.28* |
| 12 | | benzotriazolyl-CH(CH₃)- | 4-Cl-phenyl | benzyl | 9 | | 0.37 |
| 13 | | benzotriazolyl-CH(CH₃)- | 4-MeO-phenyl | benzyl | 36 | 6.4 | 0.43 |
| 14 | | benzotriazolyl-CH(CH₃)- | 3-MeO-phenyl | benzyl | 71 | 6.6 | 0.33 |
| 15 | | benzotriazolyl-CH(CH₃)- | pyridin-3-yl | benzyl | 72 | 9.7 | 0.48 |
| 16 | | benzotriazolyl-CH(CH₃)- | pyridin-4-yl | benzyl | 54 | | 0.52 |

TABLE 1A-continued

Designed Broad-Spectrum Coronaviral 3CL$^{pro}$ Inhibitors from 1P.

| Inhibitor | R-Group Substituted | R$_1$ | R$_3$ | R$_4$ | % Yield | Score | Gini Coefficient |
|---|---|---|---|---|---|---|---|
| 51 | | benzotriazolyl-CH$_2$ | 2-Cl-4-O$_2$N-phenyl | benzyl | 76 | | 0.39 |
| 52 | | benzotriazolyl-CH$_2$ | 4-Me$_2$N-phenyl | benzyl | 22 | | 0.42 |
| 54 | | benzotriazolyl-CH$_2$ | 4-Me$_2$N(H$_2$C)$_3$O-phenyl | benzyl | 30 | 19.8 | 0.59 |
| 55 | | benzotriazolyl-CH$_2$ | 4-Cl-3-F-phenyl | benzyl | 4 | 9.8 | 0.50 |
| 19 | R$_1$ | benzimidazolyl-CH$_2$ | 3-F-phenyl | benzyl | 61 | 6.8 | 0.31 |
| 20 | | benzofuranyl-CH$_2$ | 3-F-phenyl | benzyl | 61 | | 0.39 |
| 56 | | N-Boc-piperidin-4-yl | 3-F-phenyl | benzyl | 53 | | 0.34 |

TABLE 1A-continued
Designed Broad-Spectrum Coronaviral 3CL$^{pro}$ Inhibitors from 1P.
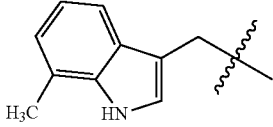 [SMILES: *Cc1c[nH]c2c(C)cccc12]
| Inhibit

TABLE 1B

Designed Broad-Spectrum Coronaviral 3CL$^{pro}$ Inhibitors from 2P.

| Inhibitor | R-Group Substituted | R$_1$ | R$_4$ | % Yield | Score | Gini Coefficient |
|---|---|---|---|---|---|---|
| 2P | N/A | benzotriazole-CH(CH$_3$)- | t-butyl | 77 | 8.5 | 0.29 |
| 24 | R$_1$ | benzothiophen-3-yl-CH(CH$_3$)- | t-butyl | 69 | | 0.40 |
| 25 | | benzofuran-3-yl-CH(CH$_3$)- | t-butyl | 69 | | 0.39 |
| 26 | | indol-3-yl-CH(CH$_3$)- | t-butyl | 76 | | 0.46 |
| 27 | | benzimidazol-1-yl-CH(CH$_3$)- | t-butyl | 65 | 11.0 | 0.37 |
| 60 | | N-Boc-piperidin-4-yl-C(CH$_3$)- | t-butyl | 74 | | 0.60 |
| 61 | | 7-methylindol-3-yl-CH(CH$_3$)- | t-butyl | 66 | | 0.43 |

TABLE 1B-continued

Designed Broad-Spectrum Coronaviral 3CL$^{pro}$ Inhibitors from 2P.

| Inhibitor | R-Group Substituted | R$_1$ | R$_4$ | % Yield | Score | Gini Coefficient |
|---|---|---|---|---|---|---|
| 62 | | 1H-benzimidazol-2-yl-ethyl | tert-butyl | 34 | | 0.46 |
| 63 | | 2-methyl-imidazol-1-yl-ethyl | tert-butyl | 74 | | 0.44 |
| 29 | R$_2$ | benzotriazol-1-yl-methyl | isopropyl | 55 | 6.3* | 0.27* |
| 30 | | benzotriazol-1-yl-methyl | isobutyl | 62 | 4.9* | 0.23* |
| 31 | | benzotriazol-1-yl-methyl | neopentyl | 68 | 6.0* | 0.25* |
| 32 | | benzotriazol-1-yl-methyl | cyclopropyl | 14 | 5.0* | 0.24* |
| 33 | | benzotriazol-1-yl-methyl | cyclopentyl | 20 | 5.7* | 0.32 |

TABLE 1B-continued

Designed Broad-Spectrum Coronaviral 3CL$^{pro}$ Inhibitors from 2P.

| Inhibitor | R-Group Substituted | R$_1$ | R$_4$ | % Yield | Score | Gini Coefficient |
|---|---|---|---|---|---|---|
| 34 | | benzotriazole-CH(CH$_3$)- | -CH$_2$-(3-pyridyl) | 83 | 4.5* | 0.21* |
| 37 | | benzotriazole-CH(CH$_3$)- | -CH$_2$-phenyl | 37 | 5.3* | 0.25* |
| 64 | | benzotriazole-CH(CH$_3$)- | -CH$_2$-C(O)O-tBu | 13 | 2.8* | 0.15* |
| 67 | | benzotriazole-CH(CH$_3$)- | -CH(CH$_3$)-cyclohexyl | 20 | 8.3* | 0.39 |

TABLE 1C

Designed Broad-Spectrum Cronaviral 3CL$^{pro}$ Inhibitors from 3P.

| Inhibitor | R-Group Substituted | R$_2$ | R$_4$ | % Yield | Score | Gini Coefficient |
|---|---|---|---|---|---|---|
| 3P | N/A | 4-tert-butylphenyl | tert-butyl | 20 | 2.7 | 0.13 |
| 38 | R$_2$ | 4-isobutylphenyl | tert-butyl | 27 | 4.5 | 0.21 |
| 39 | | 4-cyclopropylphenyl | tert-butyl | 10 | 7.6 | 0.19 |
| 40 | | 4-cyclobutylphenyl | tert-butyl | 21 | 3.6 | 0.16 |
| 41 | | 4-cyclopentylphenyl | tert-butyl | 12 | 6.2 | 0.26 |
| 42 | | 4-cyclohexylphenyl | tert-butyl | 12 | 6.6 | 0.18 |
| 69 | | 3,4,5-trimethoxyphenyl | tert-butyl | 15 | | 0.45 |
| 70 | | 4-chloro-3-methylphenyl | tert-butyl | 7 | | 0.33 |
| 71 | | 3-tert-butylphenyl | tert-butyl | 9 | | 0.30 |

TABLE 1C-continued

Designed Broad-Spectrum Coronaviral 3CL$^{pro}$ Inhibitors from 3P.

| Inhibitor | R-Group Substituted | R$_2$ | R$_4$ | % Yield | Score | Gini Coefficient |
|---|---|---|---|---|---|---|
| 43 | R$_4$ | 4-tert-butylphenyl | isobutyl | 6 | 1.9* | 0.08* |
| 44 |  | 4-tert-butylphenyl | neopentyl | 4 | 1.9* | 0.10* |
| 46 |  | 4-tert-butylphenyl | cyclopropyl | 4 | 4.0 | 0.12* |
| 47 |  | 4-tert-butylphenyl | cyclopentyl | 7 | 1.5* | 0.06* |
| 48 |  | 4-tert-butylphenyl | benzyl | 5 | 3.5 | 0.17 |
| 77 |  | 4-tert-butylphenyl | cyclohexyl | 17 | 1.4* | 0.10* |

Evaluation of Broad-Spectrum Coronaviral 3CL$^{pro}$ Inhibitors

Figure 3A:
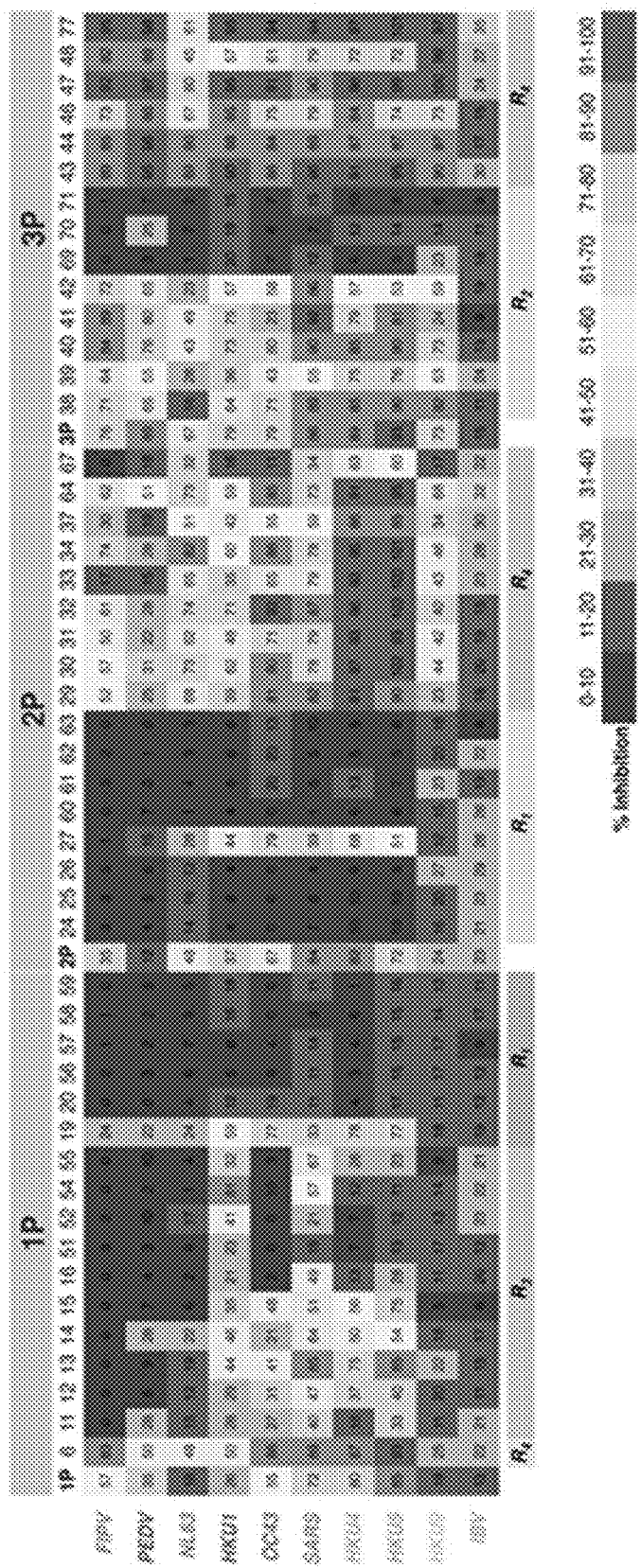
FIG. 3A is the heat map of 3CL$^{pro}$ inhibition by the designed peptidomimetic library, where the inhibitors showing above 50% inhibition of a given 3CLpro at 100 μM are shown in gradient green and those below are shown in gradient red.

Ten CoV 3CL$^{pro}$'s representing members from each of the α-, β-, and γ-phylogenetic groups and subgroups were expressed and purified to high purity to be assayed for inhibition by the designed library: FIPV-, PEDV-, and NL63-3CL$^{pro}$ from the α-CoV lineage, HKU1-, OC43-, SARS-, HKU4-, HKU5-, and HKU9-3CL$^{pro}$ from the β-CoV lineage, and IBV-3CL$^{pro}$ from the γ-CoV lineage (FIGS. 1A-1B) (St. John, et al., *Bioorg Med Chem Lett* 2015, 25(22):5072-5077; Grum-Tokars, et al., *Virus Res* 2008, 133(1):63-73). The designed library was then tested against all ten 3CL$^{pro}$'s individually to determine inhibition. Briefly, the enzymatic activity of a given 3CL$^{pro}$ in the presence of a library member at a concentration of 100 μM was measured using a synthetic FRET peptide substrate containing the consensus nsp4-nsp5 cleavage site known for 3CL$^{pro}$'s: HilyteFluor™-488-ESATLQSGLRKAK-(QXL™-520)-NH$_2$ (AnaSpec, Inc.). IC$_{50}$ values were then determined for compounds that produced greater than 50% inhibition of a given 3CL$^{pro}$ at 100 μM (FIG. 3A). These data are summarized in Table 2.

TABLE 2

Inhibition of phylogenetically distinct 3CL$^{pro}$ by designed library.

| | α | | | β | | | | | | Gini |
| | | | | 2a | | 2b | 2c | | 2d | |
| Cmpd. | FIPV | PEDV | NL63 | HKU1 | OC43 | SARS | HKU4 | HKU5 | HKU9 | Coefficient |
|---|---|---|---|---|---|---|---|---|---|---|
| IP | 6.7 ± 0.7 | | | | 6.9 ± 0.9 | 1.6 ± 0.2 | 1.1 ± 0.1 | 1.2 ± 0.1 | | 0.31 |
| 6 | 13.8 ± 1.1 | 8.3 ± 1.2 | | 6.8 ± 1.9 | 10.0 ± 1.9 | 5.5 ± 0.7 | 2.0 ± 0.1 | 2.5 ± 0.2 | | 0.22 |
| 11 | | | | | | | | | | 0.28 |
| 12 | | | | | | | | | | 0.37 |
| 13 | | | | 2.5 ± 0.4 | | 1.1 ± 0.1 | 1.1 ± 0.1 | 1.3 ± 0.2 | | 0.43 |
| 14 | | | | 1.8 ± 0.3 | | 3.5 ± 0.4 | 2.4 ± 0.2 | 2.2 ± 0.3 | | 0.33 |
| 15 | | | | | | 10.9 ± 1.9 | 4.0 ± 0.4 | 9.6 ± 1.2 | | 0.48 |
| 16 | | | | | | | | | | 0.52 |
| 51 | | | | | | | | | | 0.39 |
| 52 | | | | | | | | | | 0.42 |
| 54 | | | | 20.0 ± 2.9 | | 27.3 ± 4.6 | | | | 0.59 |
| 55 | | | | | | 0.8 ± 0.1 | | | | 0.50 |
| 19 | | | | 3.7 ± 0.6 | 3.9 ± 0.4 | | 2.5 ± 0.2 | 2.9 ± 0.3 | | 0.31 |
| 20 | | | | | | | | | | 0.39 |
| 56 | | | | | | | | | | 0.34 |
| 57 | | | | | | | | | | 0.38 |
| 58 | | | | | | | | | | 0.40 |
| 59 | | | | | | | | | | 0.44 |
| 2P | | | | | 24.4 ± 3.5 | 8.9 ± 1.4 | 3.8 ± 0.3 | 3.5 ± 0.5 | | 0.29 |
| 24 | | | | | | | | | | 0.40 |
| 25 | | | | | | | | | | 0.39 |
| 26 | | | | | | | | | | 0.46 |
| 27 | | | | | 16.3 ± 2.1 | | 9.6 ± 1.0 | 9.7 ± 1.6 | | 0.37 |
| 60 | | | | | | | | | | 0.60 |
| 61 | | | | | | | | | | 0.43 |
| 62 | | | | | | | | | | 0.46 |
| 63 | | | | | | | | | | 0.44 |
| 29 | | | 8.1 ± 1.6 | | 11.1 ± 1.2 | 8.3 ± 1.5 | 2.0 ± 0.2 | 2.4 ± 0.3 | | 0.27 |
| 30 | | | 4.2 ± 0.8 | 13.5 ± 2.8 | 2.7 ± 0.1 | 10.5 ± 1.2 | 0.6 ± 0.04 | 0.6 ± 0.1 | | 0.23 |
| 31 | | | 11.8 ± 3.5 | | 5.8 ± 0.6 | 4.2 ± 0.5 | 0.9 ± 0.1 | 1.1 ± 0.1 | | 0.25 |
| 32 | | | 14.8 ± 1.2 | 9.8 ± 1.8 | 2.8 ± 0.2 | 8.2 ± 1.5 | 0.8 ± 0.1 | 0.9 ± 0.1 | | 0.24 |
| 33 | | | 3.7 ± 0.6 | | 7.3 ± 0.8 | 4.2 ± 0.6 | 0.5 ± 0.05 | 0.6 ± 0.1 | | 0.32 |
| 34 | 27.5 ± 3.8 | | 15.6 ± 1.3 | 7.4 ± 1.1 | 8.9 ± 0.5 | 9.9 ± 0.9 | 1.1 ± 0.1 | 2.1 ± 0.2 | | 0.21 |
| 37 | | | 3.0 ± 0.3 | | 2.2 ± 0.2 | 2.0 ± 0.2 | 0.6 ± 0.04 | 0.8 ± 0.1 | | 0.25 |
| 64 | 11.7 ± 1.2 | 8.7 ± 1.4 | 8.7 ± 0.8 | 6.5 ± 0.9 | 4.5 ± 0.3 | 6.3 ± 0.8 | 2.1 ± 0.2 | 2.0 ± 0.2 | | 0.15 |
| 67 | | | | | | | 0.7 ± 0.1 | 0.6 ± 0.1 | | 0.39 |
| 3P | 33.1 ± 4.0 | 3.8 ± 0.4 | 22.3 ± 2.9 | 8.4 ± 0.7 | 13.7 ± 1.5 | 6.2 ± 0.4 | 7.0 ± 0.5 | 6.2 ± 0.8 | 38.0 ± 7.7 | 0.13 |
| 38 | 61.1 ± 13.9 | 15.5 ± 1.8 | | 15.4 ± 1.5 | 24.4 ± 3.1 | 7.0 ± 0.6 | 7.7 ± 0.7 | 10.9 ± 0.9 | 18.0 ± 3.3 | 0.21 |
| 39 | | 17.6 ± 2.6 | | 2.0 ± 1.1 | | 12.7 ± 2.5 | 16.6 ± 1.7 | 15.7 ± 2.0 | | 0.19 |
| 40 | 27.0 ± 3.1 | 11.2 ± 1.5 | | 6.6 ± 1.2 | 13.7 ± 1.3 | 9.9 ± 1.2 | 9.6 ± 0.7 | 8.7 ± 1.2 | 18.2 ± 2.2 | 0.16 |
| 41 | 18.7 ± 2.0 | 10.5 ± 0.9 | | 5.0 ± 0.6 | | 5.3 ± 0.5 | 19.8 ± 1.5 | 19.1 ± 2.0 | | 0.26 |
| 42 | 39.7 ± 5.7 | 26.2 ± 2.4 | | 11.6 ± 1.5 | 63.1 ± 12.0 | 6.3 ± 0.5 | 27.0 ± 4.1 | 4.3 ± 1.0 | | 0.18 |
| 69 | | | | | | | | | | 0.45 |
| 70 | | | | | | | | | | 0.33 |
| 71 | | | | | | | | | | 0.30 |
| 43 | 16.2 ± 1.3 | 1.6 ± 0.1 | 13.5 ± 0.8 | 5.8 ± 0.8 | 12.4 ± 1.0 | 5.9 ± 0.5 | 4.6 ± 0.3 | 5.8 ± 0.8 | 10.5 ± 1.1 | 0.08 |
| 44 | 12.5 ± 0.8 | 1.4 ± 0.1 | 8.2 ± 0.5 | 9.0 ± 0.8 | 15.6 ± 1.0 | 6.3 ± 0.5 | 4.2 ± 0.2 | 3.6 ± 0.3 | 9.1 ± 0.8 | 0.10 |
| 46 | 43.9 ± 6.1 | 4.3 ± 0.4 | 16.8 ± 2.9 | 7.8 ± 1.2 | 24.5 ± 4.3 | 11.8 ± 1.6 | 11.2 ± 1.0 | 8.9 ± 0.9 | | 0.12 |
| 47 | 6.9 ± 0.5 | 0.7 ± 0.03 | 6.3 ± 0.5 | 3.4 ± 0.4 | 7.7 ± 0.8 | 1.7 ± 0.2 | 1.9 ± 0.1 | 2.5 ± 0.2 | 6.4 ± 0.5 | 0.06 |
| 48 | 19.0 ± 1.7 | 3.4 ± 0.4 | 26.4 ± 4.2 | 8.0 ± 1.5 | 46.5 ± 8.0 | 6.6 ± 0.8 | 26.1 ± 2.1 | 24.8 ± 2.9 | 40.4 ± 8.7 | 0.17 |
| 77 | 3.3 ± 0.2 | 0.5 ± 0.04 | 5.1 ± 0.3 | 5.0 ± 0.7 | 7.0 ± 0.3 | 2.3 ± 0.1 | 1.7 ± 0.1 | 2.4 ± 0.3 | 3.6 ± 0.3 | 0.10 |

The goal in the design of the 48-member library was to identify molecules with both increased potency and broad-spectrum inhibition of CoV 3CL$^{pro}$'s. The performance of the library was assessed in two ways. First, a performance metric was developed that incorporates both potency and broad-spectrum efficacy into a single score (Equation 1). The performance metric is reminiscent of the selectivity scores used for kinases (Fedorov, et al., Proc. Natl. Acad. Sci. USA 2007, 104(51): 20523-20528), where the determined IC$_{50}$ values were used as the threshold metric, where IC$_{50}$ values were only determined for compounds that showed inhibition of a respective 3CL$^{pro}$ above 50% at 100 μM, and were averaged across 3CL$^{pro}$'s for a given compound and then divided by the number of 3CL$^{pro}$'s that IC$_{50}$'s were determined for. The number of 3CL$^{pro}$'s that IC$^{50}$'s were not determined for was then added to this number, yielding the performance metric score, which ranges from 1.4 to 19.8 for the library. Using the scoring method, compounds 1P, 2P, and 3P were determined to have scores of 5.7, 8.5, and 2.7, respectively, where the lower performance metric scores indicate better potency and broad-spectrum inhibition. Library members with scores lower than their parent compounds were considered to outperform their parent compound, therefore signifying that the substitution made to the R-group of library member increased potency and broad-spectrum 3CL$^{pro}$ inhibition (Tables 1A-1C, and Table 2). In this way, 13 compounds were identified from the 48-member library with increased performance relative to their parent compounds. Interestingly, no compound, including the parent compounds 1P, 2P, and 3P, was found to be capable of inhibiting the γ-CoV IBV-3CL$^{pro}$.

$$\text{Score} = \frac{\text{Average } IC_{50}}{\text{\# } 3CL^{pro}\text{'s with hdetermined } IC_{50}\text{'s}} + \text{\# } 3CL^{pro}\text{'s without determined } IC_{50}\text{'s}$$

Equation 1. Performance Metric for Broad-Spectrum 3CL$^{pro}$ Inhibition

Figure 3B:
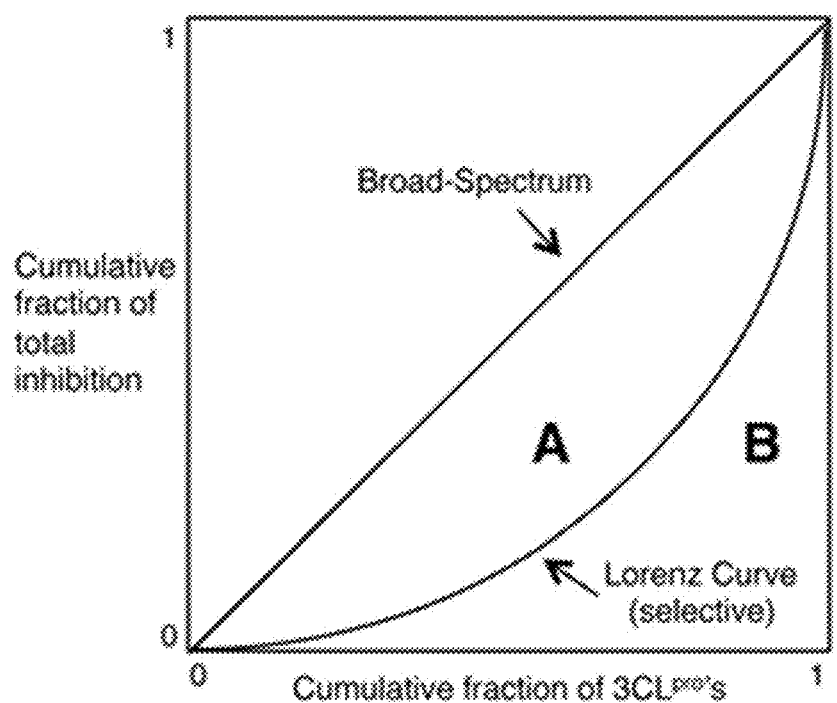
FIG. 3B is the Gini coefficient calculated as a ratio of the areas A/(A+B).
Figure 3C:
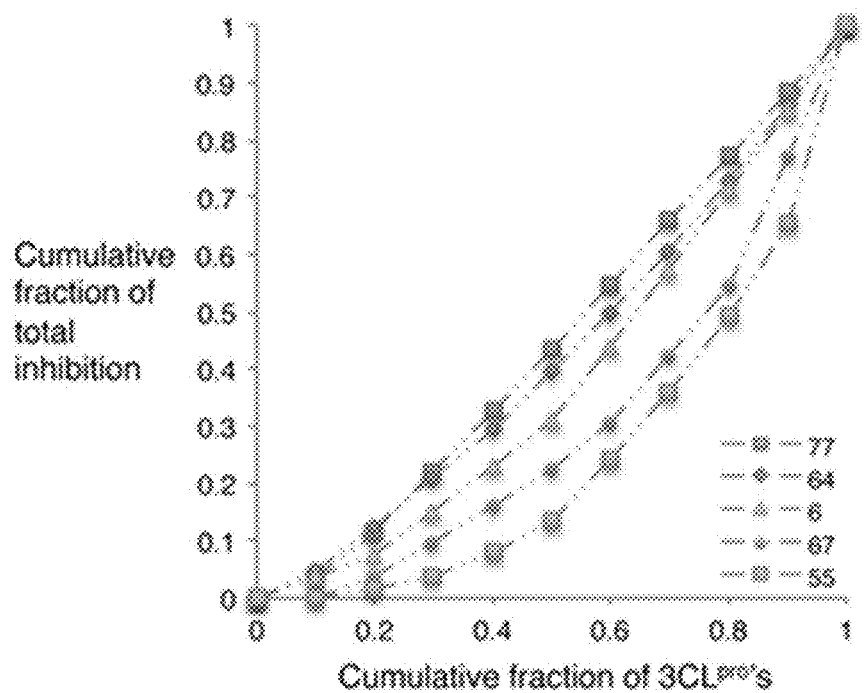
FIG. 3C shows the Gini coefficient plots for inhibitors 77, 64, 6, 67, and 55.
Figure 3D:
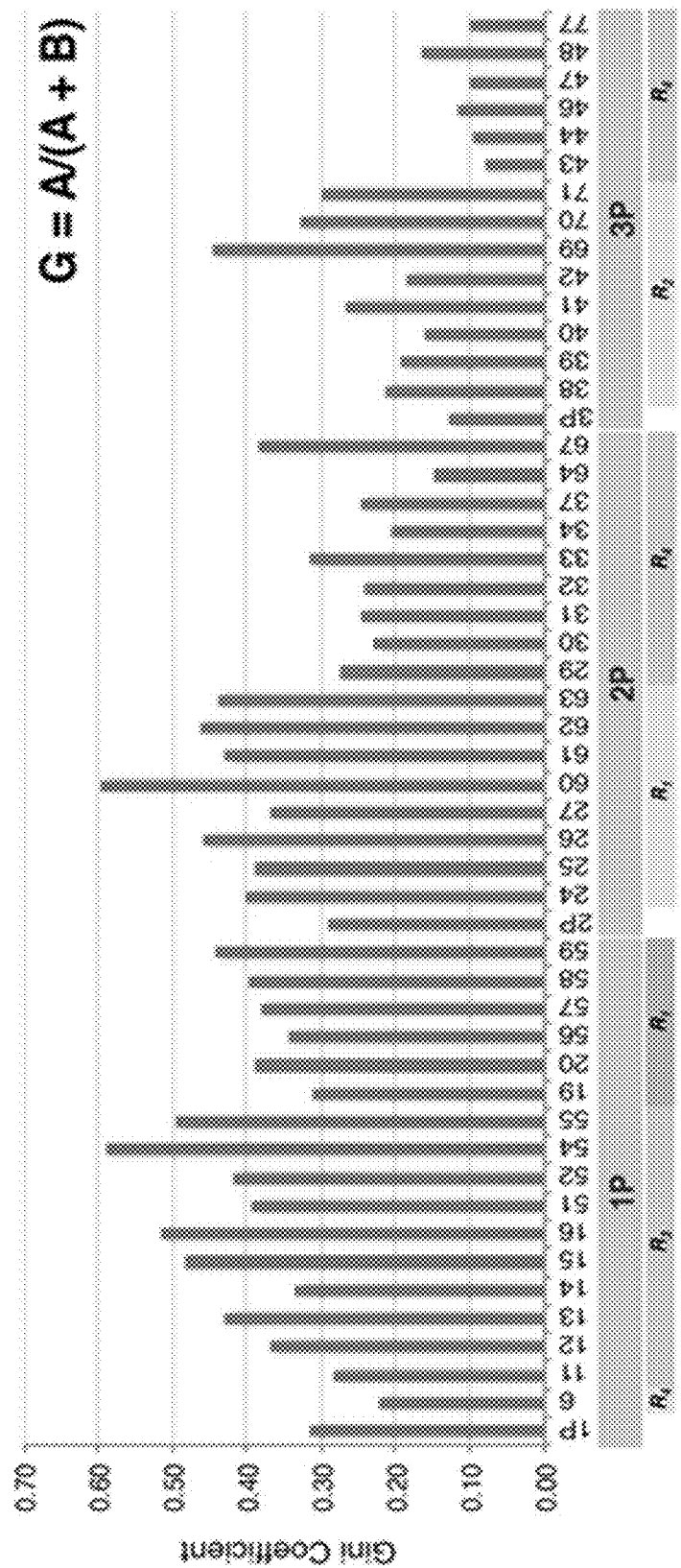
FIG. 3D is a graphical showing of the calculated Gini coefficients for each studied inhibitor in the library.

A second way to assess the performance of the broad-spectrum library was to use the Gini coefficient, which is frequently used by economists to measure income inequality, but has been previously used as a method to express selectivity of kinase inhibitors against a family of kinases (Graczyk, *J. Med. Chem.* 2007, 50(23):5773-5779; Dorfman, *Rev. Econ. Stat.* 1979, 61(1):146-149). Using the Gini coefficient, broad-spectrum inhibition was evaluated using the magnitude of inhibition measured for each 3CL$^{pro}$, yielding Gini coefficients for every compound in the library, not just the compounds showing greater than 50% inhibition of a 3CL$^{pro}$ at 100 μM (Tables 1A-1C). Briefly, the total inhibition was calculated as the sum of magnitudes of inhibition for each library member for all 3CL$^{pro}$'s tested. The percent inhibition of every 3CL$^{pro}$ by a given library member were then sorted by increasing inhibition, and the cumulative fraction of total inhibition was plotted against the cumulative fraction of 3CL$^{pro}$'s. If all 3CL$^{pro}$'s tested are inhibited similarly by a compound, the slope of this plotted line will be linear, indicating a lack of selectivity and success as a broad-spectrum inhibitor. If a compound is a selective inhibitor, this line will resemble a Lorenz curve (FIG. 3B). The Gini coefficient is then determined by taking the area between the diagonal and the Lorenz curve (termed A) and dividing it by the sum of A and B, where B is the area under the Lorenz curve (FIG. 3B). Compounds with the lowest Gini coefficients are therefore the most successful broad-spectrum inhibitors. This is illustrated by the Gini plots of compounds 77, 64, 6, 67, and 55 in FIG. 3C. A graphical illustration of the Gini coefficients for each library member is displayed in FIG. 3D.

Broad-Spectrum Performance of 1P-Based Inhibitors

Figure 4A:
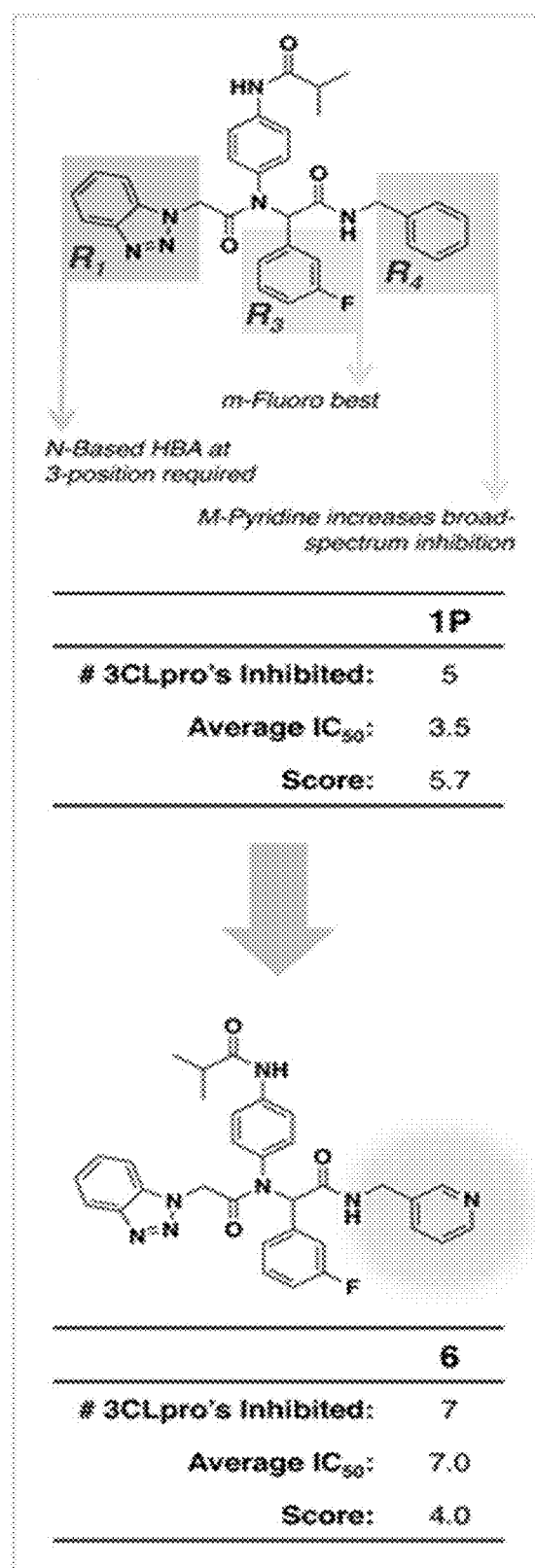
FIG. 4A shows the structure-activity relationships of peptidomimetics derived from 1P scaffold, wherein the best performing compound 6 is displayed.

Of the 17 compounds that were synthesized based on the 1P scaffold, one compound was identified that outperformed the parent compound 1P using the performance metric score and Gini coefficient, compound 6, with a performance metric score of 4.0 and a Gini coefficient of 0.22 compared to 1P, which has a score of 5.7 and Gini coefficient of 0.31. Compound 6 is the only analog synthesized in the library with an R$_4$-group substitution, having a 3-pyridylmethyl instead of an R$_4$-benzyl (Tables 1-2, FIG. 4A). This substitution increases broad-spectrum inhibitory capability, where compound 6 now inhibits both PEDV- and HKU1-3CL$^{pro}$ over 50% at 100 μM, two 3CL$^{pro}$'s that were not inhibited above 50% by the parent compound 1P at 100 μM. The addition of a nitrogen atom within the R$_4$ substituent may allow 6 to make additional electrostatic or hydrogen-bonding contacts within the 3CL$^{pro}$ binding site, therefore leading to the observed increase in broad-spectrum inhibition (FIG. 4A).

None of the substitutions made to the R$_3$-position of 1P increased potency or broad-spectrum inhibition (compounds 11-16, 51-52, 54-55) using the performance metric score, indicating that the original m-fluorophenyl substituent at this position is favored (Table 1A). Interestingly, substitution at this position is tolerated by the β-CoV 3CL$^{pro}$'s belonging to the 2a-c subgroups better than the 3CL$^{pro}$'s belonging to the α-, β-2c, and γ-CoV phylogenetic lineages, indicating a feature of 3CL$^{pro}$ active sites belonging to the β-CoV 2a-c subgroup lineages that can be exploited by these molecules. Substitution of the m-fluorophenyl of 1P for the m-chlorophenyl of compound 11 resulted in a complete loss of inhibition above 50% of any 3CL$^{pro}$ at 100 μM; however, the electron-donating and m-methoxy of compound 14 is tolerated by HKU1-, SARS-, HKU4- and HKU5-3CL$^{pro}$, with low micromolar IC$_{50}$ values against those 3CL$^{pro}$'s. The p-methoxy analog 13 has comparable inhibitory potency and broad-spectrum 3CL$^{pro}$ inhibition to compound 14 and the p-dimethylaminopropoxy analog 54 is tolerated by HKU1- and SARS-3CL$^{pro}$, but the p-dimethylamino analog 52 results in a complete loss of inhibitory activity toward any 3CL$^{pro}$ above 50% at 100 μM. The m-pyridine analog 15 was found to inhibit SARS-, HKU4-, and HKU5-3CL$^{pro}$; however, the p-pyridine analog 16 did not show inhibitory activity above 50% of any 3CL$^{pro}$ at 100 μM. Finally, the μ-chloro-m-fluoro analog 55 displays SARS-3CL$^{pro}$ selective inhibition with sub-micromolar inhibitory potency (IC$_{50}$=0.8±0.1 μM), despite that the m-chloro analog 11 resulted in a complete loss in all 3CL$^{pro}$ inhibitory activity above 50% at 100 μM (Tables 1A and 2). Taken together, these data indicate strict requirements for the R$_3$ substituent with a complex interplay between steric and electronic demands, and potentially wide variability in the position occupied by the R$_3$ substituent in the binding site of 3CL$^{pro}$'s (FIG. 4A).

Six analogs were synthesized to determine heterocycle tolerance at the R$_1$-position of 1P (compounds 19-20 and 56-59, Table 1A). Notably, compound 19 was the only analog found to retain inhibition of some 3CL$^{pro}$'s above 50% at 100 μM, where 19 has an R$_1$-benzimidazole in place of the R$_1$-benzotriazole of 1P. The R$_1$-benzofuran analog 20 showed a complete loss in inhibitory activity above 50% at 100 μM toward any 3CL$^{pro}$, despite being bioisosteric with both the R$_1$-benzotriazole and R$_1$-benzimidazole of 1P and 19, respectively. Similarly, the R$_1$-7-methylindole analog 57 showed no inhibition above 50% at 100 μM of any 3CL$^{pro}$. These data indicate that for effective broad-spectrum 3CL$^{pro}$ inhibition, a nitrogen-based hydrogen-bond acceptor is required at the 3-position of the indene ring (FIG. 4A).

Broad-Spectrum Performance of 2P-Based Inhibitors

Figure 4B:
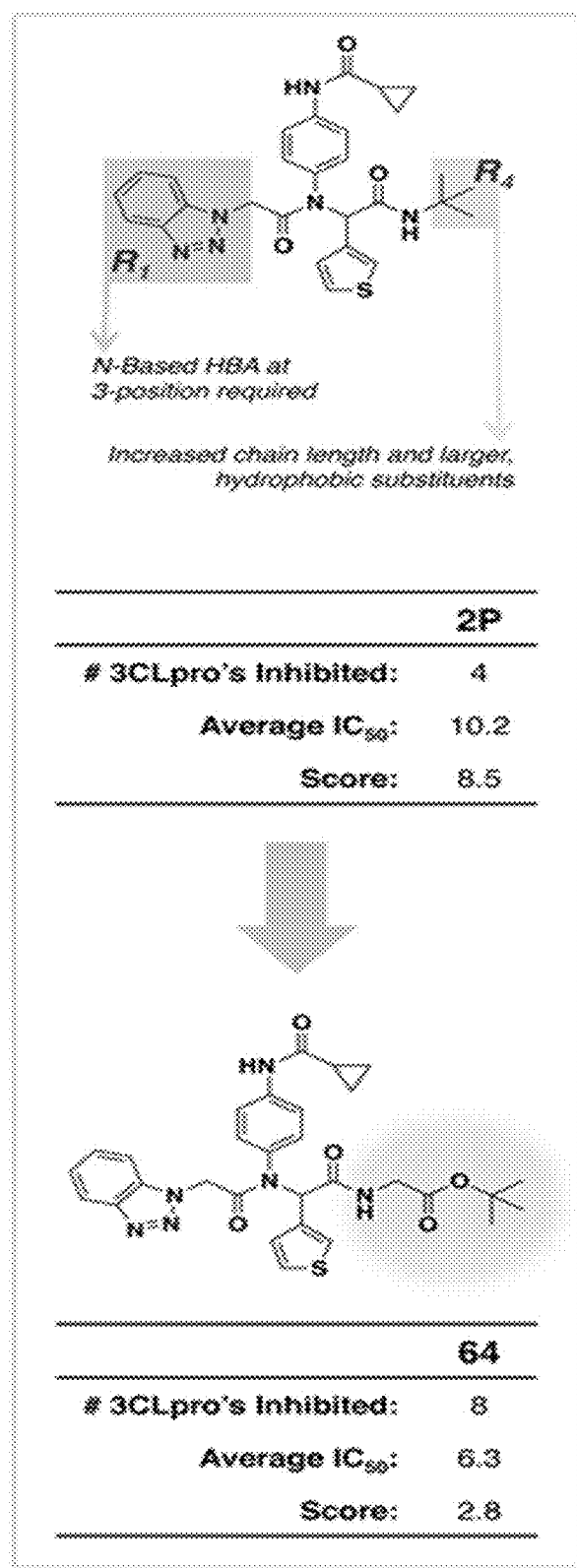
FIG. 4B shows the structure-activity relationships of peptidomimetics derived from 2P scaffold, wherein the best performing compound 64 is displayed.

Of the 17 compounds that were synthesized based on the 2P scaffold, eight compounds were identified with better inhibitory and broad-spectrum activity than the parent compound 2P based on the performance metric score (compounds 29-34, 37, and 64), which all arose from diversification at the R$_4$-position (Table 1B, FIG. 4B). Similarly to 1P, of the eight analogs of 2P with R$_1$-heterocycle variations, compounds 24-27 and 60-63, only one was found to show inhibition of 3CL$^{pro}$'s above 50% at 100 μM, compound 27, which similarly to compound 19, has an R$_1$-benzimidazole. In this series, compounds 24, 25, and 26 show that benzothiophene, benzofuran, and indole bioisosteres are not tolerated for the inhibition of any 3CL$^{pro}$ above 50% at 100 μM. Furthermore, the piperidine carbamate 60, 7-methylindole 61, 2-benzimidazole 62, and 3-methylimidazole 63, did not show inhibition of any 3CL$^{pro}$ above 50% at 100 μM. Taken together, these data indicate a strict requirement for the position the R$_1$-substituent occupies in the 3CL$^{pro}$ binding site and indicates that analogs utilizing 1P and 2P scaffolds may bind in a similar orientation, where a nitrogen-based hydrogen-bond acceptor is required at the 3-position of an indene ring (FIG. 4B).

Of the nine analogs of 2P that were synthesized to probe the effect of the $R_4$-group, eight were found to outperform the parent compound 2P (analogs 29-34, 37, and 64. See Table 1B) based on their performance metric scores. Diversification at the $R_4$-position of the 2P scaffold resulted in a set of compounds with increased broad-spectrum CoV $3CL^{pro}$ inhibition, showing inhibition of NL63-, PEDV-, and FIPV-CoV $3CL^{pro}$ above 50% at 100 µM, which is not observed in the parent compound, 2P. Generally, it was found that decreasing steric bulk at the α-position and increasing the steric bulk and hydrophobicity at the β-position of the $R_4$-substituent led to an increase in broad-spectrum activity and inhibitory potency of the analog. This is observed in the comparison of 2P to compounds 29-33 and 37, which all have decreased steric bulk at the α-position and increased bulk and hydrophobicity at the β-position of the $R_4$-chain. These data may indicate that the $R_4$-group participates in a hydrophobic or van der Waals interaction within the $3CL^{pro}$ binding site, as the increase in $R_4$ chain length and hydrophobicity results in better scoring compounds. Furthermore, the addition of a heteroatom within the $R_4$-chain leads to the two best broad-spectrum inhibitors in the 2P set, compounds 34 and 64. Compounds 34 and 64 have performance metric scores of 4.5 and 2.8, respectively, in comparison to the parent compound 2P, which has a score of 8.5. Compound 64 was found to be the best inhibitor in this set, inhibiting eight of the ten $3CL^{pro}$'s it was tested against, doubling the number of $3CL^{pro}$'s inhibited above 50% at 100 µM relative to the parent compound 2P. These data may indicate that the addition of a heteroatom allows the $R_4$-chain to pick up additional hydrogen-bonding of electrostatic interactions within the $3CL^{pro}$ binding site (FIG. 4B).

The 2P analog 67, which bears an $R_4$-cyclohexyl group, was found to be a selective sub-micromolar inhibitor of HKU4- and HKU5-$3CL^{pro}$, both of which belong to the beta-CoV subgroup 2c (Tables 1B and 2). Comparison of 67 to analogs 32 and 33 indicates that the binding pocket for the $R_4$-substituent likely varies in size and composition across $3CL^{pro}$'s, where the $R_4$-cyclohexyl of 67 is tolerated by HKU4- and HKU5-$3CL^{pro}$, which share 84.7% sequence identity, but not the other $3CL^{pro}$'s tested in the study. Compound 32, which has an $R_4$-cyclopropyl substituent, was found to be a good inhibitor of six $3CL^{pro}$'s: NL63-, HKU1-, OC43-, SARS-, HKU4- and HKU5-$3CL^{pro}$. Increasing the $R_4$-substitutent ring size from three to five carbons, as seen in the comparison of compounds 32 and 33, reduces the broad-spectrum capability of 33 and is not tolerated by HKU1-$3CL^{pro}$. Increasing the $R_4$-substituent ring size by an additional carbon, as in the $R_4$-cyclohexyl substituent of analog 67, further reduces the number of $3CL^{pro}$'s inhibited above 50% at 100 µM and is not tolerated by NL63-, OC43-, and SARS-$3CL^{pro}$, leading to an apparent selective beta-coronavirus subgroup 2c inhibitor (compound 67). These small changes in the size of the inhibitor $R_4$-substituent produce large changes in the broad-spectrum inhibition of $3CL^{pro}$'s and are inform us of subtle, but crucial, differences across CoV $3CL^{pro}$ binding sites that need to be identified.

Broad-Spectrum Performance of 3P-Based Inhibitors

Of the 14 compounds synthesized to investigate the $R_2$- and $R_4$-positions of the 3P scaffold, four compounds were identified with better inhibitory potency and broad-spectrum activity against CoV $3CL^{pro}$'s than the parent compound 3P based on their performance metric scores (compounds 43, 44, 47, and 77, Table 1C). Interestingly, just like with the 1P- and 2P-based analogs, these better performing inhibitors were identified from the set of compounds synthesized to investigate the effect of substitution at the $R_4$-position of 3P.

Figure 4C:
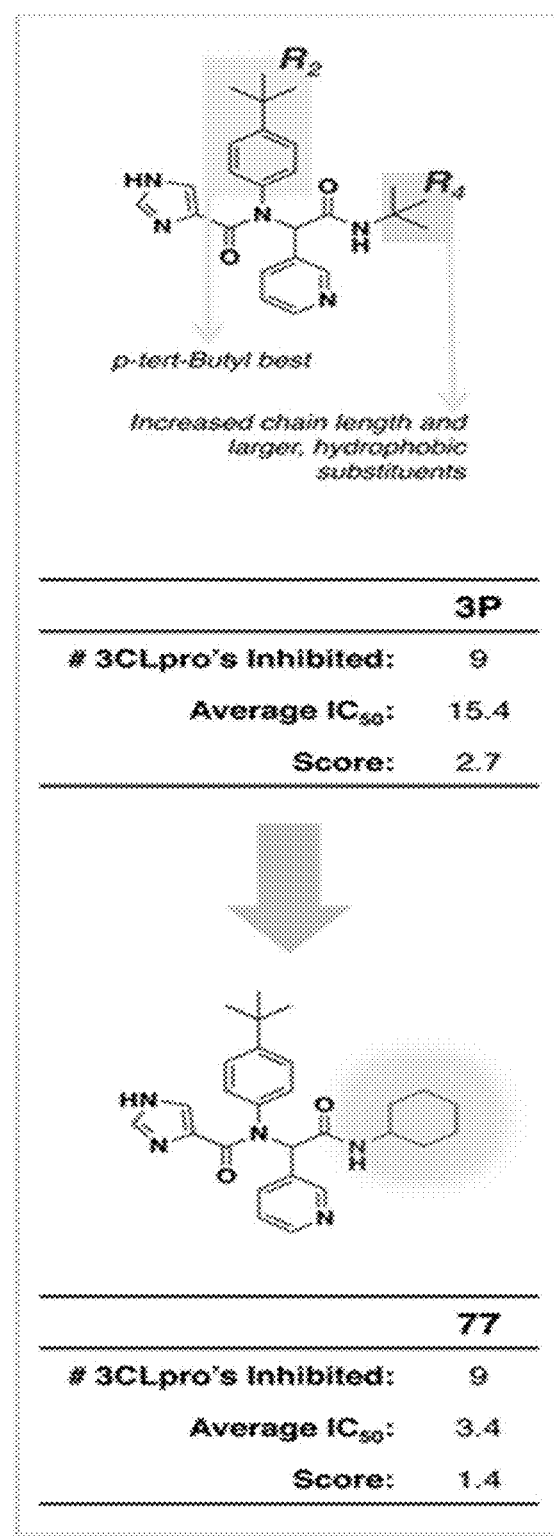
FIG. 4C shows the structure-activity relationships of peptidomimetics derived from 3P scaffold, wherein the best performing compound 77, is displayed.

To determine the steric requirements of the $R_2$ p-tertbutylphenyl of 3P, analogs 38-42 were synthesized to investigate the steric effect at the p-position of the phenyl ring. Increasing the chain length of the $R_2$ p-phenyl substituent resulted in an increased score of analog 38 relative to 3P (4.5 vs. 2.7), was not tolerated by NL63-$3CL^{pro}$, and may indicate that the position occupied by the p-phenyl group in NL63-$3CL^{pro}$ has more stringent steric requirements for binding as compared to other $3CL^{pro}$'s. The analog series 39-42 represents incremental one carbon increases in cycloalkyl ring size at the $R_2$ p-phenyl position ranging from p-cyclopropyl to p-cyclohexyl. Compound 39, having a p-cyclopropylphenyl at the $R_2$-position, the smallest and least hydrophobic substituent tested at this position, displayed the worst broad-spectrum inhibition, only inhibiting five out of ten $3CL^{pro}$'s above 50% at 100 µM. Increasing the ring size by one carbon, resulting in the p-cyclobutylphenyl analog 40, gave the best scoring analog in cycloalkyl series, inhibiting eight of ten $3CL^{pro}$'s with a performance metric score of 3.6. Interestingly, compound 40 is sterically similar to the parent compound 3P. A further increase in cycloalkyl ring size, as in p-cyclopentyl and p-cyclohexyl of compounds 41 and 42, did not result in increased potency or broad-spectrum activity, but resulted in similar performance metric scores for compounds 41 and 42, scoring 6.2 and 6.6 respectively. The effect of substituent position and identity on the $R_2$ phenyl ring was further investigated with analogs 69-71. It was found that a substitution at p-position of the $R_2$ phenyl is required for good $3CL^{pro}$ inhibition, since compounds 69-71 resulted in a complete loss in $3CL^{pro}$ inhibitory activity above 50% at 100 µM (FIG. 4C).

Compounds 43-48 and 77 were designed to investigate the requirement for the $R_4$-position of 3P (Table 1C). Gratifyingly, this series resulted in compounds with good inhibition and broad-spectrum activity toward $3CL^{pro}$'s and produced four compounds that had performance metric scores outperforming the parent 3P, analogs 43, 44, 47, and 77 (scoring 1.9, 1.9, 1.5, and 1.4, respectively). Compounds 43, 44, 47, and 77 have larger, hydrophobic groups at the $R_4$-position in comparison to the parent compound 3P, indicating they may participate in hydrophobic or van der Waals interactions with the $3CL^{pro}$ binding site. Taken together with the findings from the $R_4$-substitutions of the 1P and 2P-based scaffolds, this gives evidence that the $R_4$-substituent of the inhibitors may be located in the same position across both chemical scaffolds and $3CL^{pro}$'s. From this set, compounds 47 and 77 were identified to be the best scoring analogs synthesized in the entire 48-member library, inhibiting all α- and β-CoV $3CL^{pro}$'s against which they were tested with $IC_{50}$ values ranging from 0.5 to 8 µM across $3CL^{pro}$'s (FIG. 4C).

Structural Evaluation of Broad-Spectrum Coronaviral $3CL^{pro}$ Inhibitors

Figure 5A:
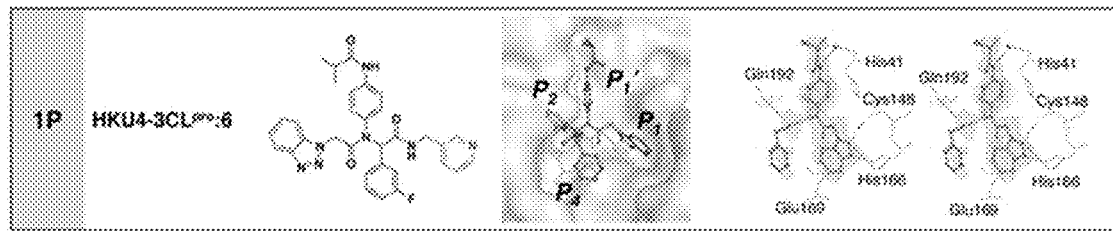
FIG. 5A is the X-Ray crystal structures of broad-spectrum inhibitors derived from 1P in complex with 3CL$^{pro}$'s. X-ray structure is represented as space-filled active site with R-group protease pockets labeled, and wall-eye stereo-view of the inhibitors in each active site. The residues of the respective 3CL$^{pro}$ active sites are shown as grey, colored according to atom type, represented as sticks, and labeled. Hydrogen-bond interactions are represented as black dashed lines. Water molecules are represented as red spheres. The electron density omit map ($F_o$-$F_c$) surrounding each inhibitor is shown in grey mesh and contoured to +2.0σ.
Figure 5B:
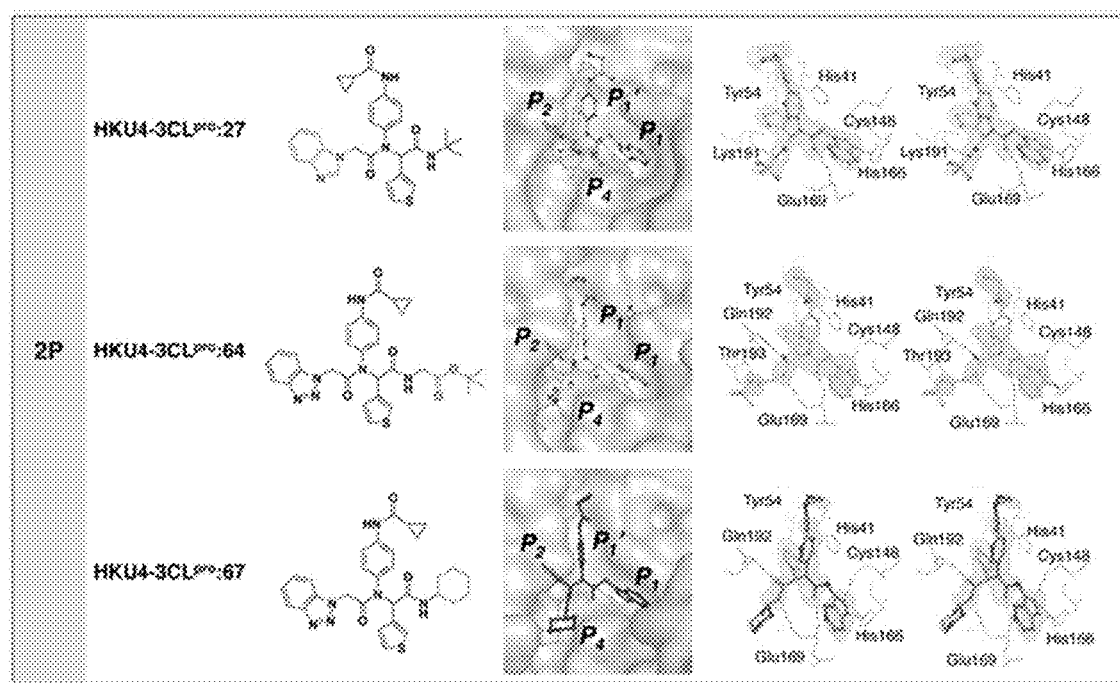
FIG. 5B is the X-Ray crystal structures of broad-spectrum inhibitors derived from 2P in complex with 3CL$^{pro}$'s. Further legend is the same as that of FIG. 5A.
Figure 5C:
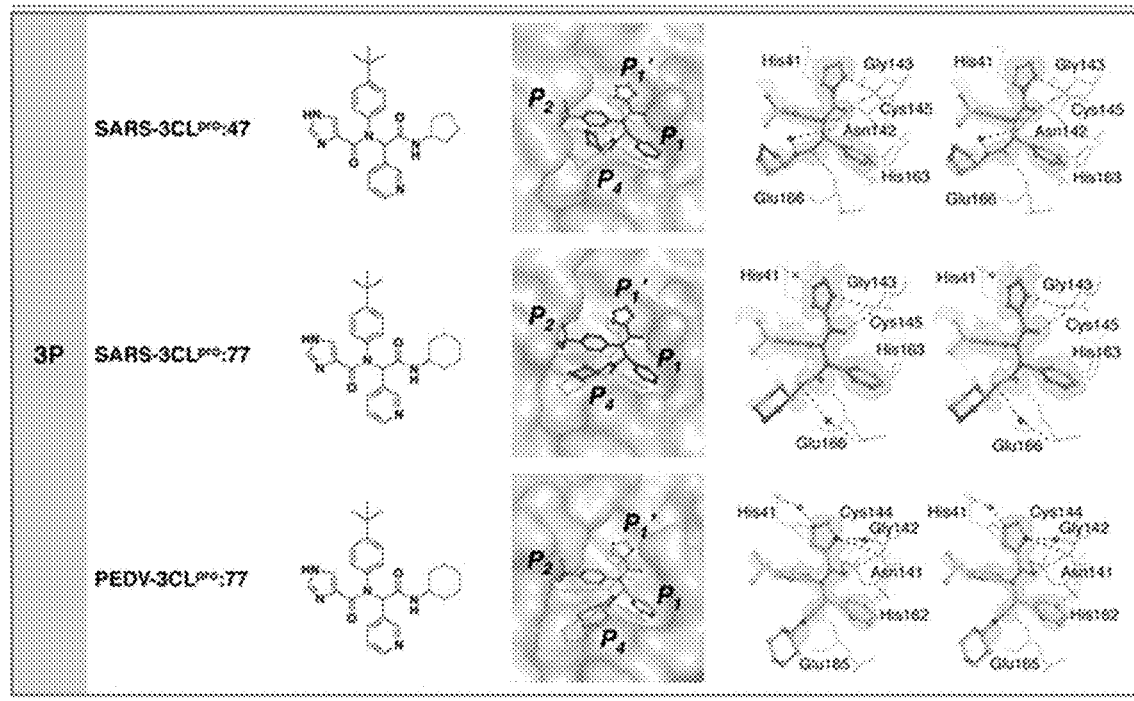
FIG. 5C is the X-Ray crystal structures of broad-spectrum inhibitors derived from 3P in complex with 3CL$^{pro}$'s. Further legend is the same as that of FIG. 5A.

To understand the structural determinants behind the trends in the inhibition data, the X-ray crystal structures of one or more compounds from each of the 1P, 2P, and 3P analog sets in complex with the α-CoV PEDV-$3CL^{pro}$, and the β-CoV SARS- and HKU4-$3CL^{pro}$'s were determined (FIGS. 5A-5C). Seven X-ray crystal structures of $3CL^{pro}$: inhibitor complexes were determined: HKU4-$3CL^{pro}$:6, HKU4-$3CL^{pro}$:27, HKU4-$3CL^{pro}$:64, HKU4-$3CL^{pro}$:67, SARS-$3CL^{pro}$:47, SARS-$3CL^{pro}$:77, and PEDV-$3CL^{pro}$:77.

The goal was to gain insights into the molecular features of the inhibitors important for broad-spectrum 3CL$^{pro}$ inhibition and to determine if the inhibitors shared a common binding orientation across chemical scaffolds and 3CL$^{pro}$'s. Another goal was to elucidate the structural and molecular basis for the increased broad-spectrum and inhibitory potency of compounds 6, 64, 47, and 77 and contrast this with the X-ray crystal structure of HKU4-3CL$^{pro}$ in complex with the lower scoring inhibitor, 27. Additionally, the X-ray crystal structure of 67 in complex with HKU4-3CL$^{pro}$ was determined to elucidate the structural and molecular basis for selective inhibition of HKU4- and HKU5-3CL$^{pro}$ inhibition by 67.

In each of the seven X-ray crystal structures that were determined, the (R)-enantiomer of each inhibitor was found in the 3CL$^{pro}$ active site, indicating a preference for the (R)-enantiomer of the racemate for 3CL$^{pro}$ inhibition, which was also observed in the X-ray crystal structures of both SARS-3CL$^{pro}$ and HKU4-3CL$^{pro}$ bound with first generation library members (Jacobs, et al., *J. Med. Chem.* 2013, 56(2):534-546). Interestingly, it was discovered that the binding orientation of the inhibitor in the 3CL$^{pro}$ active site is dependent on the R-groups of the molecular scaffold, where the analogs derived from 1P and 2P scaffolds (compounds 6, 27, 64, and 67) bind in the same orientation and the analogs derived from the 3P scaffold (compounds 47 and 77) bind in a different orientation than compounds 6, 27, 64, and 67, but in the same orientation as each other (FIGS. 5A-5C).

Examination of all seven of the determined X-ray crystal structures proved that two hydrogen-bonding interactions between the inhibitor molecules and residues in each 3CL$^{pro}$ active site are conserved (FIGS. 5A-5C). These two conserved hydrogen-bonds are formed between the inhibitor molecule and His166, 162, or 163 and Glu169, 165, or 166 of HKU4-, PEDV-, or SARS-3CL$^{pro}$, respectively. Compound 6, from the 1P compound family, and compounds 27, 64, and 67, from the 2P compound family, all bind in the same orientation and participate in a 2.8-2.9 Å hydrogen-bonding interaction from the tele-NH of His166 in HKU4-3CL$^{pro}$ to the 3-nitrogen of the benzimidazole or benzotriazole ring of the inhibitor R$_1$-substituent. This hydrogen-bonding interaction is conserved in the X-ray structures of compounds 47 and 77, which are based off the 3P scaffold and bind in a different orientation than 6, 27, 64, and 67, in both SARS- and PEDV-3CL$^{pro}$, where the tele-NH of His162 or His163 in PEDV- or SARS-3CL$^{pro}$, respectively, forms a 2.8-2.9 Å hydrogen-bond to the pyridine-nitrogen of the R$_3$-substituent of compounds 47 and 77.

Experimental Procedures

General Procedure for the Synthesis of Broad-Spectrum Inhibitors:

Equimolar amounts of amine, aldehyde, and acid in MeOH (0.2 M) were added to a 1-dram vial containing a magnetic stir bar and allowed to stir at ambient temperature for 30 minutes. The isocyanide (0.90 eq.) was then added. The reaction vessel was allowed to stir for 18 hours at ambient temperature before it was diluted with MeOH, filtered through a celite pad, and purified by HPLC.

N-(4-(2-(1H-benzo[d][1,2,3]triazol-1-yl)-N-(1-(3-fluorophenyl)-2-oxo-2-((pyridin-3-ylmethyl)amino)ethyl)acetamido)phenyl)isobutyramide (6)

$^1$H NMR (400 MHz, DMSO-d$_6$) δ (ppm): 9.92 (s, 1H), 8.80 (t, J=5.9 Hz, 1H), 8.40 (dd, J=4.8, 1.7 Hz, 2H), 8.05 (dt, J=8.4, 0.9 Hz, 1H), 7.73 (dt, J=8.4, 0.9 Hz, 1H), 7.64-7.37 (m, 5H), 7.29-7.16 (m, 2H), 7.08-6.90 (m, 3H), 6.03 (s, 1H), 5.33 (d, J=17.3 Hz, 1H), 5.22 (d, J=17.3 Hz, 1H), 4.34 (d, J=5.8 Hz, 2H), 2.60-2.53 (m, 1H), 1.07 (d, J=6.8 Hz, 6H). ESI-MS(+): 580.2 [M+1].

N-(4-(2-(1H-benzo[d][1,2,3]triazol-1-yl)-N-(2-(benzylamino)-1-(3-chlorophenyl)-2-oxoethyl)acetamido)phenyl)isobutyramide (11)

$^1$H NMR (400 MHz, DMSO-d$_6$) δ (ppm): 9.93 (s, 1H), 8.73 (t, J=5.9 Hz, 1H), 8.05 (dt, J=8.4, 0.9 Hz, 1H), 7.74 (dt, J=8.4, 1.0 Hz, 1H), 7.64-7.46 (m, 3H), 7.42 (ddd, J=8.2, 7.0, 1.0 Hz, 1H), 7.31-7.00 (m, 9H), 6.04 (s, 1H), 5.34 (d, J=17.2 Hz, 1H), 5.21 (d, J=17.3 Hz, 1H), 4.45-4.18 (m, 2H), 2.62-2.53 (m, 1H), 1.08 (d, J=6.8 Hz, 6H). ESI-MS(+): 595.2 [M+1].

N-(4-(2-(1H-benzo[d][1,2,3]triazol-1-yl)-N-(2-(benzylamino)-1-(4-chlorophenyl)-2-oxoethyl)acetamido)phenyl)isobutyramide (12)

$^1$H NMR (400 MHz, DMSO-d$_6$) δ (ppm): 9.93 (s, 1H), 9.38 (s, 1H), 8.69 (t, J=5.9 Hz, 1H), 8.05 (dt, J=8.5, 1.0 Hz, 1H), 7.78-7.68 (m, 1H), 7.55 (ddd, J=8.2, 6.9, 1.0 Hz, 2H), 7.42 (ddd, J=8.0, 6.9, 1.0 Hz, 1H), 7.32-7.24 (m, 2H), 7.24-7.10 (m, 8H), 6.53-6.44 (m, 1H), 6.05 (s, 1H), 5.33 (d, J=17.3 Hz, 1H), 5.20 (d, J=17.2 Hz, 1H), 4.36-4.23 (m, 2H), 2.60-2.53 (m, 1H), 1.08 (d, 7.9 Hz, 6H). ESI-MS(+): 595.2 [M+1].

N-(4-(2-(1H-benzo[d][1,2,3]triazol-1-yl)-N-(2-(benzylamino)-1-(4-methoxyphenyl)-2-oxoethyl)acetamido)phenyl)isobutyramide (13)

$^1$H NMR (400 MHz, DMSO-d$_6$) δ (ppm): 9.91 (s, 1H), 8.59 (t, J=5.9 Hz, 1H), 8.05 (d, J=8.4 Hz, 1H), 7.73 (d, J=8.4 Hz, 1H), 7.60-7.50 (m, 2H), 7.47-7.36 (m, 2H), 7.27-7.10 (m, 5H), 7.03 (d, J=8.7 Hz, 2H), 6.74 (d, J=8.7 Hz, 2H), 6.00 (s, 1H), 5.31 (d, J=17.2 Hz, 1H), 5.17 (d, J=17.2 Hz, 1H), 4.42-4.19 (m, 2H), 3.67 (s, 3H), 2.60-2.53 (m, 1H), 1.08 (d, J=6.8 Hz, 6H). ESI-MS(+): 591.3 [M+1].

N-(4-(2-(1H-benzo[d][1,2,3]triazol-1-yl)-N-(2-(benzylamino)-1-(3-methoxyphenyl)-2-oxoethyl)acetamido)phenyl)isobutyramide (14)

$^1$H NMR (400 MHz, DMSO-d$_6$) δ (ppm): 9.91 (s, 1H), 8.66 (t, J=6.0 Hz, 1H), 8.05 (dt, J=8.4, 0.9 Hz, 1H), 7.74 (dt, J=8.5, 1.0 Hz, 1H), 7.55 (ddd, J=8.2, 6.9, 1.0 Hz, 2H), 7.42 (ddd, J=8.1, 6.9, 1.0 Hz, 1H), 7.27-7.12 (m, 5H), 7.09 (dd, J=8.5, 7.3 Hz, 1H), 6.77-6.66 (m, 3H), 6.01 (s, 1H), 5.33 (d, J=17.2 Hz, 1H), 5.19 (d, J=17.2 Hz, 1H), 4.36 (dd, J=15.2, 6.0 Hz, 1H), 4.25 (dd, J=15.2, 5.7 Hz, 1H), 3.61 (s, 3H), 2.63-2.54 (m, 1H), 1.07 (d, J=6.8 Hz, 6H). ESI-MS(+): 591.3 [M+1].

N-(4-(2-(1H-benzo[d][1,2,3]triazol-1-yl)-N-(2-(benzylamino)-2-oxo-1-(pyridin-3-yl)ethyl)acetamido)phenyl)isobutyramide (15)

$^1$H NMR (400 MHz, DMSO-d$_6$) δ (ppm): 9.94 (s, 1H), 8.75 (t, J=5.9 Hz, 1H), 8.41-8.30 (m, 2H), 8.05 (d, J=8.4 Hz, 1H), 7.75 (d, J=8.3 Hz, 1H), 7.63-7.47 (m, 3H), 7.47-7.37 (m, 2H), 7.27-7.07 (m, 6H), 6.09 (s, 1H), 5.35 (d, J=17.3 Hz, 1H), 5.23 (d, J=17.3 Hz, 1H), 4.40-4.22 (m, 2H), 2.61-2.53 (m, 1H), 1.07 (d, J=6.8 Hz, 6H). ESI-MS(+): 562.2 [M+1].

N-(4-(2-(1H-benzo[d][1,2,3]triazol-1-yl)-N-(2-(benzylamino)-2-oxo-1-(pyridin-4-yl)ethyl)acetamido)phenyl)isobutyramide (16)

$^1$H NMR (400 MHz, DMSO-d$_6$) δ (ppm): 9.94 (s, 1H), 8.78 (t, J=5.8 Hz, 1H), 8.41 (s, 2H), 8.05 (d, J=8.4 Hz, 1H), 7.74 (d, J=8.3 Hz, 1H), 7.55 (t, J=7.3 Hz, 3H), 7.47 ? 7.36 (m, 2H), 7.30 ? 7.06 (m, 7H), 6.04 (s, 1H), 5.38 (d, J=17.3 Hz, 1H), 5.24 (d, J=17.3 Hz, 1H), 4.44 ? 4.21 (m, 2H), 2.60 ? 2.54 (m, 1H), 1.08 (d, J=6.8 Hz, 6H). ESI-MS(+): 562.2 [M+1].

N-(4-(2-(1H-benzo[d]imidazol-1-yl)-N-(2-(benzylamino)-1-(3-fluorophenyl)-2-oxoethyl)acetamido)phenyl)isobutyramide (19)

$^1$H NMR (400 MHz, DMSO-d$_6$) δ (ppm): 9.92 (s, 1H), 8.72 (t, J=5.9 Hz, 1H), 8.08 (s, 1H), 7.72-7.60 (m, 1H), 7.54 (s, 2H), 7.43-7.36 (m, 1H), 7.29-7.11 (m, 8H), 7.07-6.99 (m, 1H), 6.99-6.88 (m, 2H), 6.06 (s, 1H), 4.82 (d, J=17.3 Hz, 1H), 4.73 (d, J=17.3 Hz, 1H), 4.41-4.22 (m, 2H), 2.60-2.54 (m, 1H), 1.07 (d, J=6.7 Hz, 6H). ESI-MS(+): 578.2 [M+1].

N-(4-(2-(benzofuran-3-yl)-N-(2-(benzylamino)-1-(3-fluorophenyl)-2-oxoethyl)acetamido)phenyl)isobutyramide (20)

$^1$H NMR (400 MHz, DMSO-d$_6$) δ (ppm): 9.85 (s, 1H), 8.72 (t, J=5.9 Hz, 1H), 7.73 (s, 1H), 7.60-7.35 (m, 5H), 7.35-7.25 (m, 2H), 7.25-7.15 (m, 7H), 7.06-6.85 (m, 4H), 6.11 (s, 1H), 4.33 (d, J=5.8 Hz, 2H), 2.58-2.52 (m, 1H), 1.06 (d, J=6.8 Hz, 6H). ESI-MS(+): 578.2 [M+1].

N-(4-(2-(benzo[b]thiophen-3-yl)-N-(2-(tert-butylamino)-2-oxo-1-(thiophen-3-yl)ethyl)acetamido)phenyl)cyclopropanecarboxamide (24)

$^1$H NMR (400 MHz, DMSO-d$_6$) δ (ppm): 10.18 (s, 1H), 8.00-7.87 (m, 1H), 7.69 (s, 1H), 7.64-7.55 (m, 1H), 7.51-7.29 (m, 5H), 7.25 (dd, J=5.0, 2.9 Hz, 1H), 7.17 (dd, J=3.0, 1.2 Hz, 1H), 6.74-6.67 (m, 1H), 6.06 (s, 1H), 3.60 (d, J=16.5 Hz, 1H), 3.50 (d, J=16.1 Hz, 1H), 1.72 (p, J=6.1 Hz, 1H), 1.24 (s, 9H), 0.76 (d, J=6.1 Hz, 4H). ESI-MS(+): 546.2 [M+1].

N-(4-(2-(benzofuran-3-yl)-N-(2-(tert-butylamino)-2-oxo-1-(thiophen-3-yl)ethyl)acetamido)phenyl)cyclopropanecarboxamide (25)

$^1$H NMR (400 MHz, DMSO-d$_6$) δ (ppm): 10.20 (s, 1H), 7.70 (d, J=5.4 Hz, 2H), 7.56-7.46 (m, 2H), 7.46-7.35 (m, 2H), 7.35-7.23 (m, 2H), 7.23-7.13 (m, 2H), 6.75-6.64 (m, 1H), 6.06 (s, 1H), 3.44 (d, J=16.6 Hz, 1H), 3.34-3.30 (m, 1H), 1.73 (p, J=6.2 Hz, 1H), 1.24 (s, 9H), 0.77 (d, J=6.2 Hz, 4H). ESI-MS(+): 530.2 [M+1].

N-(4-(N-(2-(tert-butylamino)-2-oxo-1-(thiophen-3-yl)ethyl)-2-(1H-indol-3-yl)acetamido)phenyl)cyclopropanecarboxamide (26)

$^1$H NMR (400 MHz, DMSO-d$_6$) δ (ppm): 10.82 (s, 1H), 10.19 (s, 1H), 7.64 (s, 1H), 7.40 (s, 2H), 7.34 (d, J=7.9 Hz, 1H), 7.30 (d, J=8.0 Hz, 1H), 7.24 (dd, J=5.0, 2.9 Hz, 1H), 7.15 (dd, J=2.9, 1.2 Hz, 1H), 7.09-6.98 (m, 2H), 6.96-6.86 (m, 1H), 6.69 (dd, J=5.0, 1.2 Hz, 1H), 6.06 (s, 1H), 3.41 (d, J=16.0 Hz, 1H), 3.33 (d, J=16.0 Hz, 1H), 1.73 (p, J=6.3 Hz, 1H), 0.86-0.67 (d, J=6.3 Hz, 4H). ESI-MS(+): 529.2 [M+1].

N-(4-(2-(1H-benzo[d]imidazol-1-yl)-N-(2-(tert-butylamino)-2-oxo-1-(thiophen-3-yl)ethyl)acetamido)phenyl)cyclopropanecarboxamide (27)

$^1$H NMR (400 MHz, DMSO-d$_6$) δ (ppm): 10.26 (s, 1H), 8.07 (s, 1H), 7.71 (s, 1H), 7.67-7.58 (m, 1H), 7.50 (s, 2H), 7.40-7.31 (m, 1H), 7.28 (dd, J=5.0, 2.9 Hz, 1H), 7.20 (ddd, J=7.0, 5.1, 1.8 Hz, 3H), 6.74 (dd, J=5.1, 1.3 Hz, 1H), 6.02 (s, 1H), 4.82 (d, J=17.3 Hz, 1H), 4.68 (d, J=17.4 Hz, 1H), 1.75 (p, J=6.2 Hz, 1H), 1.22 (s, 9H), 0.78 (d, J=6.2 Hz, 4H). ESI-MS(+): 530.2 [M+1].

N-(4-(2-(1H-benzo[d][1,2,3]triazol-1-yl)-N-(2-(isopropylamino)-2-oxo-1-(thiophen-3-yl)ethyl)acetamido)phenyl)cyclopropanecarboxamide (29)

$^1$H NMR (400 MHz, DMSO-d$_6$) δ (ppm): 10.27 (s, 1H), 8.04 (d, J=8.4 Hz, 1H), 7.95 (d, J=7.6 Hz, 1H), 7.74 (d, J=8.4 Hz, 1H), 7.60-7.44 (m, 3H), 7.44-7.37 (m, 1H), 7.30 (dd, J=4.9, 3.0 Hz, 1H), 7.24 (d, J=2.3 Hz, 1H), 6.74 (d, J=5.0 Hz, 1H), 5.99 (s, 1H), 5.33 (d, J=17.2 Hz, 1H), 5.17 (d, J=17.2 Hz, 1H), 3.87 (dq, J=13.4, 6.6 Hz, 1H), 1.75 (p, J=6.2 Hz, 1H), 1.01 (d, J=6.6 Hz, 3H), 0.96 (dd, J=6.6 Hz, 3H), 0.79 (d, J=6.2 Hz, 4H). ESI-MS(+): 517.2 [M+1].

N-(4-(cyclopropanecarboxamido)phenyl)-N-(2-(isobutylamino)-2-oxo-1-(thiophen-3-yl)ethyl)-1H-benzo[d][1,2,3]triazole-1-carboxamide (30)

$^1$H NMR (400 MHz, DMSO-d$_6$) δ (ppm): 10.28 (s, 1H), 8.07 (t, J=5.9 Hz, 1H), 8.03 (dd, J=8.3, 1.0 Hz, 1H), 7.73 (dd, J=8.3, 1.1 Hz, 1H), 7.54 (ddd, J=11.6, 6.5, 3.1 Hz, 3H), 7.43-7.37 (m, 1H), 7.29 (dd, J=4.9, 3.0 Hz, 1H), 7.26 (dd, J=2.9, 1.3 Hz, 1H), 6.70 (dd, J=4.9, 1.3 Hz, 1H), 6.03 (s, 1H), 5.32 (d, J=17.2 Hz, 1H), 5.18 (d, J=17.2 Hz, 1H), 2.96 (dt, J=13.0, 6.5 Hz, 1H), 2.88-2.73 (m, 1H), 1.75 (p, J=6.2 Hz, 1H), 1.63 (hept, J=6.7 Hz, 1H), 0.79 (d, J=6.1 Hz, 4H), 0.73 (dd, J=6.8, 5.0 Hz, 6H). ESI-MS(+): 531.2 [M+1].

N-(4-(cyclopropanecarboxamido)phenyl)-N-(2-(neopentylamino)-2-oxo-1-(thiophen-3-yl)ethyl)-1H-benzo[d][1,2,3]triazole-1-carboxamide (31)

$^1$H NMR (400 MHz, DMSO-d$_6$) δ (ppm): 10.28 (s, 1H), 8.08-7.93 (m, 2H), 7.75-7.66 (m, 1H), 7.62-7.44 (m, 3H), 7.44-7.35 (m, 1H), 7.31-7.22 (m, 2H), 6.70 (dd, J=4.9, 1.3 Hz, 1H), 6.09 (s, 1H), 5.32 (d, J=17.2 Hz, 1H), 5.17 (d, J=17.2 Hz, 1H), 2.96 (dd, J=13.1, 6.6 Hz, 1H), 2.82 (dd, J=13.1, 5.9 Hz, 1H), 1.75 (p, J=6.2 Hz, 1H), 0.79 (d, J=6.1 Hz, 4H), 0.73 (s, 9H). ESI-MS(+): 545.2 [M+1].

N-(4-(2-(1H-benzo[d][1,2,3]triazol-1-yl)-N-(2-(cyclopropylamino)-2-oxo-1-(thiophen-3-yl)ethyl)acetamido)phenyl)cyclopropanecarboxamide (32)

$^1$H NMR (400 MHz, DMSO-d$_6$) δ (ppm): 10.28 (s, 1H), 8.18 (d, J=4.1 Hz, 1H), 8.04 (dt, J=8.3, 0.9 Hz, 1H), 7.74 (dt, J=8.3, 0.9 Hz, 1H), 7.62 ? 7.45 (m, 3H), 7.41 (ddd, J=8.1, 6.9, 1.0 Hz, 1H), 7.30 (dd, J=5.0, 2.9 Hz, 1H), 7.23 (dd, J=2.9, 1.3 Hz, 1H), 6.72 (dd, J=5.0, 1.2 Hz, 1H), 5.94 (s, 1H), 5.32 (d, J=17.2 Hz, 1H), 5.18 (d, J=17.2 Hz, 1H), 2.62

(tq, J=7.7, 3.9 Hz, 1H), 1.75 (p, J=6.2 Hz, 1H), 0.79 (d, J=6.1 Hz, 4H), 0.63-0.53 (m, 2H), 0.36-0.24 (m, 2H). ESI-MS(+): 515.2 [M+1].

N-(4-(2-(1H-benzo[d][1,2,3]triazol-1-yl)-N-(2-(cyclopentylamino)-2-oxo-1-(thiophen-3-yl)ethyl)acetamido)phenyl)cyclopropanecarboxamide (33)

$^1$H NMR (400 MHz, DMSO-d$_6$) δ (ppm): 10.28 (s, 1H), 8.05 (d, J=7.1, 1H), 8.00 (d, J=8.4, 1H), 7.79-7.69 (m, 1H), 7.61-7.43 (m, 3H), 7.40 (ddd, J=8.0, 6.9, 0.9 Hz, 1H), 7.29 (dd, J=5.0, 3.0 Hz, 1H), 7.22 (dd, J=3.1, 1.2 Hz, 1H), 6.74 (dd, J=5.0, 1.2 Hz, 1H), 6.00 (s, 1H), 5.33 (d, J=17.2 Hz, 1H), 5.16 (d, J=17.2 Hz, 1H), 4.00 (h, J=6.7 Hz, 1H), 1.75 (dqt, J=11.2, 8.2, 4.6 Hz, 3H), 1.64-1.39 (m, 4H), 1.35 (dt, J=12.8, 6.4 Hz, 1H), 1.28-1.14 (m, 1H), 0.79 (d, J=6.1 Hz, 4H). ESI-MS(+): 543.2 [M+1].

N-(4-(2-(1H-benzo[d][1,2,3]triazol-1-yl)-N-(2-oxo-2-((pyridin-3-ylmethyl)amino)-1-(thiophen-3-yl)ethyl)acetamido)phenyl)cyclopropanecarboxamide (34)

$^1$H NMR (400 MHz, DMSO-d$_6$) δ (ppm): 10.29 (s, 1H), 8.69 (t, J=5.9 Hz, 1H), 8.39 (s, 2H), 8.05 (d, J=8.4 Hz, 1H), 7.73 (d, J=8.3 Hz, 1H), 7.54 (t, J=7.7 Hz, 4H), 7.46-7.35 (m, 1H), 7.35-7.24 (m, 2H), 7.20 (dd, J=7.7, 4.8 Hz, 1H), 6.71 (d, J=5.8 Hz, 1H), 6.07 (s, 1H), 5.34 (d, J=17.2 Hz, 1H), 5.22 (d, J=17.2 Hz, 1H), 4.33 (d, J=5.8 Hz, 2H), 1.75 (p, J=6.2 Hz, 1H), 0.79 (d, J=6.1 Hz, 4H). ESI-MS(+): 566.2 [M+1].

N-(4-(2-(1H-benzo[d][1,2,3]triazol-1-yl)-N-(2-(benzylamino)-2-oxo-1-(thiophen-3-yl)ethyl)acetamido)phenyl)cyclopropanecarboxamide (37)

$^1$H NMR (400 MHz, DMSO-d$_6$) δ (ppm): 10.29 (s, 1H), 8.62 (t, J=5.9 Hz, 1H), 8.05 (d, J=8.3 Hz, 1H), 7.74 (d, J=8.3 Hz, 1H), 7.62-7.46 (m, 4H), 7.46-7.37 (m, 1H), 7.37-7.24 (m, 2H), 7.24-7.09 (m, 5H), 6.72 (d, J=4.9 Hz, 1H), 6.10 (s, 1H), 5.34 (d, J=17.2 Hz, 1H), 5.22 (d, J=17.2 Hz, 1H), 4.42-4.21 (m, 2H), 1.75 (p, J=6.2 Hz, 1H), 0.79 (d, J=6.1 Hz, 4H). ESI-MS(+): 565.2 [M+1].

N-(2-(tert-butylamino)-2-oxo-1-(pyridin-3-yl)ethyl)-N-(4-isobutylphenyl)-1H-imidazole-4-carboxamide (38)

$^1$H NMR (400 MHz, DMSO-d$_6$) δ (ppm): 12.80 (s, 1H), 8.39-8.23 (m, 2H), 7.91 (s, 1H), 7.60 (s, 1H), 7.38 (dt, J=8.2, 2.0 Hz, 1H), 7.12 (dd, J=7.9, 4.7 Hz, 3H), 6.90 (d, J=8.2 Hz, 1H), 6.63 (s, 1H), 6.15 (s, 1H), 5.14 (s, 1H), 2.39 (d, J=7.2 Hz, 2H), 1.74 (dh, J=13.2, 6.7 Hz, 1H), 1.24 (s, 10H), 0.78 (dd, J=6.7, 3.5 Hz, 7H). ESI-MS(+): 434.2 [M+1].

N-(2-(tert-butylamino)-2-oxo-1-(pyridin-3-yl)ethyl)-N-(4-cyclopropylphenyl)-1H-imidazole-4-carboxamide (39)

$^1$H NMR (400 MHz, DMSO-d$_6$) δ (ppm): 12.50 (s, 1H), 8.33 (dd, J=4.7, 1.7 Hz, 2H), 7.90 (s, 1H), 7.59 (s, 1H), 7.40 (dt, J=7.9, 2.0 Hz, 1H), 7.16 (dd, J=7.9, 4.8 Hz, 1H), 6.92 (s, 2H), 6.17 (s, 1H), 5.17 (s, 1H), 2.55 (s, 1H), 1.85 (tt, J=8.4, 5.1 Hz, 1H), 1.24 (s, 8H), 0.94 (dt, J=9.0, 3.3 Hz, 2H), 0.61 (tt, J=4.8, 2.6 Hz, 2H). ESI-MS(+): 418.2 [M+1].

N-(2-(tert-butylamino)-2-oxo-1-(pyridin-3-yl)ethyl)-N-(4-cyclobutylphenyl)-1H-imidazole-4-carboxamide (40)

$^1$H NMR (400 MHz, DMSO-d$_6$) δ (ppm): 12.66 (s, 1H), 8.32 (dd, J=4.6, 1.7 Hz, 2H), 7.92 (s, 1H), 7.58 (s, 1H), 7.40 (dt, J=8.0, 1.9 Hz, 1H), 7.15 (dd, J=7.9, 4.8 Hz, 1H), 7.09 (s, 2H), 6.18 (s, 1H), 5.20 (s, 1H), 3.46 (dd, J=9.5, 7.6 Hz, 1H), 2.25 (dtd, J=0.2, 7.8, 3.0 Hz, 2H), 2.12-1.85 (m, 3H), 1.77 (dt, J=11.5, 7.1 Hz, 1H), 1.24 (s, 9H). ESI-MS(+): 432.2 [M+1].

N-(2-(tert-butylamino)-2-oxo-1-(pyridin-3-yl)ethyl)-N-(4-cyclopentylphenyl)-1H-imidazole-4-carboxamide (41)

$^1$H NMR (400 MHz, DMSO-d$_6$) δ (ppm): 12.80 (s, 1H), 8.43-8.21 (m, 2H), 7.90 (s, 1H), 7.60 (s, 1H), 7.39 (dt, J=8.0, 1.9 Hz, 1H), 7.15 (dd, J=7.9, 4.8 Hz, 1H), 7.01 (s, 1H), 6.16 (s, 1H), 5.09 (s, 1H), 2.93 (p, J=9.0 Hz, 1H), 1.96 (q, J=10.6 Hz, 4H), 1.85-1.63 (m, 2H), 1.68-1.51 (m, 3H), 1.43 (h, J=7.9 Hz, 2H), 1.23 (s, 9H). ESI-MS(+): 446.2 [M+1].

N-(2-(tert-butylamino)-2-oxo-1-(pyridin-3-yl)ethyl)-N-(4-cyclohexylphenyl)-1H-imidazole-4-carboxamide (42)

$^1$H NMR (400 MHz, DMSO-d$_6$) δ (ppm): 12.78 (s, 1H), 8.49-8.19 (m, 2H), 7.89 (s, 1H), 7.59 (s, 1H), 7.38 (dt, J=8.0, 1.9 Hz, 1H), 7.13 (dd, J=7.9, 4.8 Hz, 2H), 7.07 (s, 1H), 6.16 (s, 1H), 5.08 (s, 1H), 2.48-2.35 (m, 1H), 1.87-1.59 (m, 5H), 1.44-1.27 (m, 4H), 1.23 (s, 10H). ESI-MS(+): 460.2 [M+1].

N-(4-(tert-butyl)phenyl)-N-(2-(isobutylamino)-2-oxo-1-(pyridin-3-yl)ethyl)-1H-imidazole-4-carboxamide (43)

$^1$H NMR (400 MHz, DMSO-d$_6$) δ (ppm): 8.41-8.29 (m, 2H), 8.24 (t, J=5.8 Hz, 1H), 7.59 (s, 1H), 7.38 (d, J=8.0 Hz, 1H), 7.26 (s, 2H), 7.14 (dd, J=7.9, 4.8 Hz, 1H), 6.19 (s, 1H), 2.93 (dq, J=17.1, 6.6 Hz, 2H), 1.67 (hept, J=6.7 Hz, 1H), 1.22 (s, 9H), 0.78 (dd, J=6.7, 2.9 Hz, 6H). ESI-MS(+): 434.2 [M+1].

N-(4-(tert-butyl)phenyl)-N-(2-(neopentylamino)-2-oxo-1-(pyridin-3-yl)ethyl)-1H-imidazole-4-carboxamide (44)

$^1$H NMR (400 MHz, DMSO-d$_6$) δ (ppm): 12.79 (s, 1H), 8.39-8.34 (m, 1H), 8.33 (dd, J=4.8, 1.6 Hz, 1H), 8.18 (t, J=5.8 Hz, 1H), 7.59 (s, 1H), 7.38 (d, J=8.0 Hz, 1H), 7.26 (s, 2H), 7.13 (dd, J=7.9, 4.8 Hz, 1H), 6.23 (s, 1H), 5.10 (s, 1H), 3.09-2.84 (m, 2H), 1.22 (s, 9H), 0.78 (s, 9H). ESI-MS(+): 448.2 [M+1].

N-(4-(tert-butyl)phenyl)-N-(2-(cyclopropylamino)-2-oxo-1-(pyridin-3-yl)ethyl)-1H-imidazole-4-carboxamide (46)

$^1$H NMR (400 MHz, DMSO-d$_6$) δ (ppm): 12.79 (s, 1H), 8.34 (q, J=3.9, 2.9 Hz, 2H), 7.61 (s, 1H), 7.38 (dt, J=8.0, 2.0 Hz, 1H), 7.29 (s, 2H), 7.14 (dd, J=7.9, 4.6 Hz, 1H), 7.03 (s, 1H), 6.08 (s, 1H), 5.11 (s, 1H), 2.65 (dt, J=8.0, 4.0 Hz, 1H), 1.23 (s, 9H), 0.69-0.53 (m, 2H), 0.43-0.20 (m, 2H). ESI-MS(+): 418.2 [M+1].

N-(4-(tert-butyl)phenyl)-N-(2-(cyclopentylamino)-2-oxo-1-(pyridin-3-yl)ethyl)-1H-imidazole-4-carboxamide (47)

¹H NMR (400 MHz, DMSO-d₆) δ (ppm): 8.40-8.29 (m, 2H), 8.21 (d, J=7.1 Hz, 1H), 7.59 (s, 1H), 7.39 (dt, J=8.0, 2.0 Hz, 1H), 7.26 (s, 2H), 7.14 (dd, J=7.9, 4.8 Hz, 1H), 6.17 (s, 1H), 5.27 (s, 1H), 4.03 (h, J=6.7 Hz, 1H), 1.89-1.67 (m, 2H), 1.67-1.33 (m, 5H), 1.22 (s, 10H). ESI-MS(+): 446.2 [M+1].

N-(2-(benzylamino)-2-oxo-1-(pyridin-3-yl)ethyl)-N-(4-(tert-butyl)phenyl)-1H-imidazole-4-carboxamide (48)

¹H NMR (400 MHz, DMSO-d₆) δ (ppm): 12.82 (s, 1H), 8.77 (dt, J=7.0, 3.7 Hz, 1H), 8.45-8.26 (m, 2H), 7.61 (s, 1H), 7.39 (dd, J=8.4, 2.9 Hz, 1H), 7.35-7.29 (m, 1H), 7.29-7.18 (m, 4H), 7.14 (dd, J=7.9, 4.8 Hz, 1H), 6.23 (s, 1H), 5.12 (s, 1H), 4.47-4.24 (m, 2H), 1.23 (s, 9H). ESI-MS(+): 468.2 [M+1].

N-(4-(2-(1H-benzo[d][1,2,3]triazol-1-yl)-N-(2-(benzylamino)-1-(2-chloro-5-nitrophenyl)-2-oxoethyl)acetamido)phenyl)isobutyramide (51)

¹H NMR (400 MHz, DMSO-d₆) δ (ppm): 9.92 (s, 1H), 9.05 (t, J=5.9 Hz, 1H), 8.11 (dd, J=8.8, 2.7 Hz, 1H), 8.06 (dt, J=8.4, 0.9 Hz, 1H), 7.79 (d, J=8.8 Hz, 1H), 7.75 (d, J=2.8 Hz, 1H), 7.72 (dt, J=8.3, 1.0 Hz, 1H), 7.61-7.49 (m, 3H), 7.42 (ddd, J=8.1, 6.9, 1.0 Hz, 1H), 7.27-7.13 (m, 7H), 6.42 (s, 1H), 5.54 (d, J=17.3 Hz, 1H), 5.23 (d, J=17.3 Hz, 1H), 4.44 (dd, J=15.1, 6.1 Hz, 1H), 4.27 (dd, J=15.1, 5.5 Hz, 1H), 2.54 (d, J=8.5 Hz, 1H), 1.05 (d, J=7.0 Hz, 6H). ESI-MS(+): 640.2 [M+1].

N-(4-(2-(1H-benzo[d][1,2,3]triazol-1-yl)-N-(2-(benzylamino)-1-(4-(dimethylamino)phenyl)-2-oxoethyl)acetamido)phenyl)isobutyramide (52)

¹H NMR (400 MHz, DMSO-d₆) δ (ppm): 9.91 (s, 1H), 8.50 (t, J=6.0 Hz, 1H), 8.04 (dt, J=8.3, 0.9 Hz, 1H), 7.73 (dt, J=8.3, 1.0 Hz, 1H), 7.54 (ddd, J=8.2, 6.9, 1.0 Hz, 2H), 7.41 (ddd, J=8.1, 6.9, 1.0 Hz, 1H), 7.25-7.09 (m, 5H), 6.96-6.81 (m, 2H), 6.56-6.40 (m, 2H), 5.94 (s, 1H), 5.29 (d, J=17.2 Hz, 1H), 5.15 (d, J=17.2 Hz, 1H), 4.40-4.18 (m, 2H), 2.82 (s, 6H), 2.60-2.53 (m, 1H), 1.08 (d, J=6.7 Hz, 6H). ESI-MS(+): 604.2 [M+1].

N-(4-(2-(1H-benzo[d][1,2,3]triazol-1-yl)-N-(2-(benzylamino)-1-(4-(3-(dimethylamino)propoxy)phenyl)-2-oxoethyl)acetamido)phenyl)isobutyramide (54)

¹H NMR (400 MHz, DMSO-d₆) δ (ppm): 9.91 (s, 1H), 8.59 (t, J=6.0 Hz, 1H), 8.05 (d, J=8.4 Hz, 1H), 7.73 (d, J=8.4 Hz, 0H), 7.55 (ddd, J=8.2, 6.9, 1.0 Hz, 3H), 7.41 (ddd, J=8.1, 6.9, 1.0 Hz, 1H), 7.26-7.10 (m, 5H), 7.07-6.97 (m, 2H), 6.79-6.65 (m, 2H), 5.99 (s, 1H), 5.30 (d, J=17.2 Hz, 1H), 5.17 (d, J=17.2 Hz, 1H), 4.29 (qd, J=15.3, 5.9 Hz, 2H), 3.90 (t, J=6.4 Hz, 2H), 2.61-2.53 (m, 1H), 2.29 (t, J=7.1 Hz, 2H), 1.77 (p, J=6.7 Hz, 2H), 1.08 (d, J=6.8 Hz, 6H). ESI-MS(+): 662.2 [M+1].

N-(4-(2-(1H-benzo[d][1,2,3]triazol-1-yl)-N-(2-(benzylamino)-1-(4-chloro-3-fluorophenyl)-2-oxoethyl)acetamido)phenyl)isobutyramide (55)

¹H NMR (400 MHz, DMSO-d₆) δ (ppm): 9.95 (s, 1H), 8.73 (t, J=5.9 Hz, 1H), 8.05 (d, J=8.3, 1.0 Hz, 1H), 7.73 (dt, J=8.3, 0.9 Hz, 1H), 7.65-7.50 (m, 3H), 7.50-7.37 (m, 2H), 7.27-7.09 (m, 6H), 6.99 (dd, J=8.3, 1.9 Hz, 1H), 6.04 (s, 1H), 5.33 (d, J=17.3 Hz, 1H), 5.23 (d, J=17.3 Hz, 1H), 4.41-4.19 (m, 2H), 2.57 (q, J=6.9 Hz, 1H), 1.08 (d, J=6.9 Hz, 6H). ESI-MS(+): 613.2 [M+1].

tert-butyl 4-((2-(benzylamino)-1-(3-fluorophenyl)-2-oxoethyl)(4-isobutyramidophenyl)carbamoyl) piperidine-1-carboxylate (56)

¹H NMR (400 MHz, DMSO-d₆) δ (ppm): 9.85 (s, 1H), 8.64 (t, J=5.9 Hz, 1H), 7.81-7.31 (m, 3H), 7.31-7.12 (m, 6H), 7.08-6.92 (m, 1H), 6.92-6.79 (m, 2H), 6.68 (s, 1H), 6.03 (s, 1H), 4.37 (dd, J=15.3, 6.0 Hz, 1H), 4.27 (dd, J=15.3, 5.7 Hz, 1H), 3.83 (s, 2H), 2.41 (s, 2H), 2.22 (ddt, J=11.2, 8.1, 3.9 Hz, 1H), 1.70-1.41 (m, 4H), 1.38 (s, 9H), 1.06 (d, J=6.8 Hz, 6H). ESI-MS(+): 531.2 [M+1].

N-(4-(N-(2-(benzylamino)-1-(3-fluorophenyl)-2-oxoethyl)-2-(7-methyl-1H-indol-3-yl)acetamido)phenyl)isobutyramide (57)

¹H NMR (400 MHz, DMSO-d₆) δ (ppm): 10.81 (d, J=3.0 Hz, 1H), 9.83 (s, 1H), 8.68 (t, J=6.0 Hz, 1H), 7.70-7.29 (m, 3H), 7.29-7.10 (m, 7H), 7.06 (d, J=2.4 Hz, 1H), 7.03-6.91 (m, 2H), 6.91-6.80 (m, 3H), 6.11 (s, 1H), 4.33 (d, J=5.8 Hz, 2H), 3.44-3.37 (m, 2H), 2.43 (s, 3H), 1.06 (d, J=6.8 Hz, 6H). ESI-MS(−): 589.0 [M+1].

3-(1H-benzo[d]imidazol-2-yl)-N-(2-(benzylamino)-1-(3-fluorophenyl)-2-oxoethyl)-N-(4-isobutyramidophenyl)propanamide (58)

¹H NMR (400 MHz, DMSO-d₆) δ (ppm): 9.87 (s, 1H), 8.68 (t, J=6.0 Hz, 1H), 7.75 (dt, J=7.3, 3.6 Hz, 2H), 7.63-7.37 (m, 4H), 7.37-7.30 (m, 1H), 7.30 ? 7.23 (m, 1H), 7.23-7.06 (m, 6H), 6.99 (td, J=8.5, 2.5 Hz, 1H), 6.93-6.79 (m, 2H), 6.01 (s, 1H), 4.36-4.24 (m, 2H), 3.24 (t, J=7.0 Hz, 2H), 2.66 (qt, J=17.3, 7.0 Hz, 2H), 1.07 (d, J=6.8 Hz, 6H). ESI-MS(+): 592.2 [M+1].

N-(2-(benzylamino)-1-(3-fluorophenyl)-2-oxoethyl)-N-(4-isobutyramidophenyl)-3-(2-methyl-1H-imidazol-1-yl)propanamide (59)

¹H NMR (400 MHz, DMSO-d₆) δ (ppm): 9.83 (s, 1H), 8.71 (t, J=5.9 Hz, 1H), 7.39 (s, 2H), 7.32-7.25 (m, 2H), 7.25-7.14 (m, 4H), 6.99 (tdd, J=8.8, 2.9, 0.9 Hz, 1H), 6.91 (d, J=1.3 Hz, 1H), 6.90-6.84 (m, 1H), 6.81 (dt, J=11.0, 1.9 Hz, 1H), 6.66 (d, J=1.3 Hz, 1H), 6.07 (s, 1H), 4.33 (d, J=5.9 Hz, 2H), 4.15-3.90 (m, 2H), 2.54 (q, J=6.7 Hz, 1H), 2.44-2.24 (m, 2H), 2.17 (s, 3H), 1.05 (d, J=6.7 Hz, 6H). ESI-MS(+): 556.2 [M+1].

tert-butyl 4-((2-(tert-butylamino)-2-oxo-1-(thiophen-3-yl)ethyl)(4-cyclopropanecarboxamido)phenyl)carbamoyl)piperidine-1-carboxylate (60)

¹H NMR (400 MHz, DMSO-d₆) δ (ppm): 10.20 (s, 1H), 7.63 (s, 1H), 7.59 (s, 1H), 7.47 (s, 1H), 7.34 (d, J=9.3 Hz, 1H), 7.23 (dd, J=5.0, 2.9 Hz, 1H), 7.12 (dd, J=3.0, 1.2 Hz, 1H), 6.65 (dd, J=4.9, 1.3 Hz, 2H), 5.98 (s, 1H), 3.83 (s, 2H), 2.39 (s, 1H), 2.18 (dq, J=11.1, 3.7 Hz, 1H), 1.73 (p, J=6.2 Hz, 1H), 1.60-1.42 (m, 3H), 1.37 (s, 9H), 1.23 (s, 9H), 0.77 (d, J=6.1 Hz, 4H). ESI-MS(−): 581.0 [M+1].

N-(4-(N-(2-(tert-butylamino)-2-oxo-1-(thiophen-3-yl)ethyl)-2-(7-methyl-1H-indol-3-yl)acetamido)phenyl)cyclopropanecarboxamide (61)

$^1$H NMR (400 MHz, DMSO-$d_6$) δ (ppm): 10.79 (d, J=2.6 Hz, 1H), 10.18 (s, 1H), 7.64 (s, 1H), 7.39 (s, 2H), 7.24 (dd, J=5.0, 2.9 Hz, 1H), 7.15 (td, J=3.8, 3.1, 1.2 Hz, 2H), 7.01 (d, J=2.4 Hz, 1H), 6.90-6.74 (m, 2H), 6.68 (dd, J=5.0, 1.2 Hz, 1H), 6.06 (s, 1H), 3.44-3.37 (m, 2H), 2.42 (s, 3H), 1.72 (p, J=6.2 Hz, 1H), 1.24 (s, 9H), 0.77 (d, J=6.1 Hz, 4H). ESI-MS(+): 543.2 [M+1].

N-(4-(3-(1H-benzo[d]imidazol-2-yl)-N-(2-(tert-butylamino)-2-oxo-1-(thiophen-3-yl)ethyl)propanamido)phenyl)cyclopropanecarboxamide (62)

$^1$H NMR (400 MHz, DMSO-$d_6$) δ (ppm): 12.08 (s, 1H), 10.18 (s, 1H), 7.66 (s, 1H), 7.52-7.44 (m, 1H), 7.39-7.34 (m, 1H), 7.27-7.20 (m, 1H), 7.14 (dd, J=3.1, 1.2 Hz, 1H), 7.13-7.02 (m, 2H), 6.68 (dd, J=5.0, 1.3 Hz, 1H), 6.03 (s, 1H), 3.08-2.87 (m, 2H), 2.61-2.53 (m, 1H), 2.40 (ddd, J=16.0, 8.7, 6.4 Hz, 1H), 1.72 (p, J=6.2 Hz, 1H), 1.24 (s, 9H), 0.83-0.64 (m, 4H). ESI-MS(+): 544.2 [M+1].

N-(4-(N-(2-(tert-butylamino)-2-oxo-1-(thiophen-3-yl)ethyl)-3-(2-methyl-1H-imidazol-1-yl)propanamido)phenyl)cyclopropanecarboxamide (63)

$^1$H NMR (400 MHz, DMSO-$d_6$) δ (ppm): 10.17 (s, 1H), 7.68 (s, 1H), 7.36 (s, 2H), 7.23 (dd, J=5.0, 2.9 Hz, 1H), 7.09 (dd, J=2.9, 1.2 Hz, 1H), 6.89 (d, J=1.4 Hz, 1H), 6.65 (d, J=1.2 Hz, 1H), 6.62 (dd, J=5.0, 1.2 Hz, 1H), 6.02 (s, 1H), 4.03 (hept, J=7.2 Hz, 2H), 2.43-2.21 (m, 2H), 2.15 (s, 3H), 1.71 (p, J=6.2 Hz, 1H), 1.24 (s, 9H), 0.76 (d, J=6.1 Hz, 4H). ESI-MS(+): 508.2 [M+1].

tert-butyl (2-(2-(1H-benzo[d][1,2,3]triazol-1-yl)-N-(4-(cyclopropanecarboxamido)phenyl)acetamido)-2-(thiophen-3-yl)acetyl)glycinate (64)

$^1$H NMR (400 MHz, DMSO-$d_6$) δ (ppm): 10.30 (s, 1H), 8.44 (d, J=6.8 Hz, 1H), 8.03 (dd, J=8.4, 1.0 Hz, 1H), 7.84-7.68 (m, 1H), 7.54 (ddd, J=10.0, 5.7, 2.4 Hz, 3H), 7.40 (ddd, J=8.0, 6.9, 1.0 Hz, 1H), 7.35 (t, J=1.9 Hz, 1H), 7.32 (dd, J=5.0, 3.0 Hz, 1H), 6.78 (dd, J=5.0, 1.2 Hz, 1H), 6.15 (s, 1H), 5.35 (d, J=17.2 Hz, 1H), 5.18 (d, J=17.3 Hz, 1H), 3.95-3.75 (m, 1H), 3.65 (dd, J=17.5, 3.3 Hz, 1H), 1.75 (p, J=6.2 Hz, 1H), 1.37 (s, 9H), 0.79 (d, J=6.1 Hz, 4H). ESI-MS(+): 589.2 [M+1].

N-(4-(2-(1H-benzo[d][1,2,3]triazol-1-yl)-N-(2-(cyclohexylamino)-2-oxo-1-(thiophen-3-yl)ethyl)acetamido)phenyl)cyclopropanecarboxamide (67)

$^1$H NMR (400 MHz, DMSO-$d_6$) δ (ppm): 10.27 (s, 1H), 8.04 (dd, J=8.4, 1.0 Hz, 1H), 7.94 (d, J=7.7 Hz, 1H), 7.73 (d, J=8.3 Hz, 1H), 7.61-7.52 (m, 2H), 7.44-7.37 (m, 1H), 7.34-7.26 (m, 1H), 7.23 (dd, J=3.0, 1.2 Hz, 1H), 6.79-6.68 (m, 1H), 6.01 (s, 1H), 5.33 (d, J=17.2 Hz, 1H), 5.16 (d, J=17.2 Hz, 1H), 3.55 (dqt, J=9.3, 5.6, 3.6 Hz, 1H), 1.89-1.45 (m, 6H), 1.35-0.90 (m, 5H), 0.79 (d, J=6.1 Hz, 4H). ESI-MS(+): 557.2 [M+1].

N-(2-(tert-butylamino)-2-oxo-1-(pyridin-3-yl)ethyl)-N-(3,4,5-trimethoxyphenyl)-1H-imidazole-4-carboxamide (69)

$^1$H NMR (400 MHz, DMSO-$d_6$) δ (ppm): 9.00 (s, 1H), 8.47 (d, J=2.1 Hz, 1H), 8.45 ? 8.36 (m, 1H), 8.03 (s, 1H), 7.56 (dt, J=8.2, 1.9 Hz, 1H), 7.28 (dd, J=7.9, 4.9 Hz, 1H), 6.14 (s, 1H), 5.86 (s, 1H), 5.77 (s, 1H), 3.60 (s, 6H), 3.17 (s, 3H), 1.26 (s, 9H). ESI-MS(+): 468.2 [M+1].

N-(2-(tert-butylamino)-2-oxo-1-(pyridin-3-yl)ethyl)-N-(4-chloro-3-methylphenyl)-1H-imidazole-4-carboxamide (70)

$^1$H NMR (400 MHz, DMSO-$d_6$) δ (ppm): 8.39-8.29 (m, 2H), 7.99 (s, 1H), 7.60 (d, J=0.8 Hz, 1H), 7.43 (dt, J=8.0, 2.0 Hz, 1H), 7.27 (d, J=8.2 Hz, 1H), 7.19 (ddd, J=7.9, 4.8, 0.8 Hz, 1H), 6.20 (s, 1H), 2.55 (s, 9H), 2.17 (s, 3H), 1.24 (s, 9H). ESI-MS(+): 426.2 [M+1].

N-(3-(tert-butyl)phenyl)-N-(2-(tert-butylamino)-2-oxo-1-(pyridin-3-ethyl)-1H-imidazole-4-carboxamide (71)

$^1$H NMR (400 MHz, DMSO-$d_6$) δ (ppm): 8.33 (d, J=2.2 Hz, 1H), 7.94 (s, 1H), 7.58 (d, J=0.8 Hz, 1H), 7.38 (dt, J=8.0, 2.0 Hz, 1H), 7.28-7.20 (m, 1H), 7.18 (s, 1H), 6.19 (s, 1H), 5.26 (s, 1H), 1.25 (s, 9H), 1.09 (s, 9H). ESI-MS(+): 434.2 [M+1].

N-(4-(tert-butyl)phenyl)-N-(2-(cyclohexylamino)-2-oxo-1-(pyridin-3-yl)ethyl)-1H-imidazole-4-carboxamide (77)

$^1$H NMR (400 MHz, DMSO-$d_6$) δ (ppm): 8.40-8.29 (m, 2H), 8.13 (d, J=7.7 Hz, 1H), 7.58 (s, 1H), 7.39 (dt, J=7.9, 2.0 Hz, 1H), 7.36-7.15 (m, 3H), 7.14 (dd, J=7.9, 4.8 Hz, 1H), 6.19 (s, 1H), 5.27 (s, 1H), 3.58 (ddt, J=10.5, 6.6, 3.4 Hz, 1H), 1.83-1.45 (m, 5H), 1.41-1.24 (m, 3H), 1.22 (s, 9H), 1.20-0.91 (m, 3H). ESI-MS(+): 460.2 [M+1].

Protein Expression and Purification

The genes encoding for the 3CL$^{pro}$'s of FIPV-, PEDV-, NL63-, HKU1-, OC43-, SARS-, HKU4-, HKU5-, HKU9-, and IBV-3CL$^{pro}$ were codon optimized for expression in *Escherichia coli* and cloned into a pET-11a expression vector with an N-terminal (His)$_6$-tag followed by nsp4-/5 auto-cleavage site by BioBasic Inc. This construct results in the expression of the 3CL$^{pro}$ of interest without an N-terminal or C-terminal extension. *E. coli* BL21 (DE3) cells, transformed with pET11a-CoV 3CL$^{pro}$ plasmid were grown in Super LB or LB media in the presence of carbenicillin. The cells were harvested by centrifugation and the cell pellet was resuspended in the appropriate buffer for purification, homogenized, and lysed. Purification was accomplished by multiple chromatographic steps starting with a Phenyl Sepharose 6 Fast Flow HiSub column, followed by a DEAE Sepharose Fast Flow column, and subsequent Mono S or Mono Q column depending on the 3CL$^{pro}$. Purified protein was flash frozen using liquid nitrogen in 25 mM HEPES pH 7.5, 2.5 mM DTT, 10% glycerol and stored at −80° C. until further use. Detailed methods for each 3CL$^{pro}$ purified can be found in the Supplemental Information.

IC$_{50}$ Determination

The inhibitor library was first screened for inhibition of each 3CL$^{pro}$ at a concentration of 100 μM in duplicate assays containing the following assay buffer (50 mM HEPES, 0.1 mg/mL BSA, 0.01% TritonX-100, 1 mM DTT). The assays were carried out in Costar 3694 EIA/RIA 96-Well Half Area, Flat Bottom, Black Polystyrene plates from Corning Incorporated. 1 μL of 100× inhibitor stock in DMSO was added to 79 μL of enzyme in assay buffer and the enzyme-inhibitor mixture was incubated for 10 minutes. The reaction was initiated by the addition of 20 μL of 10 μM UIVT3 substrate, a custom synthesized Förster resonance energy transfer substrate peptide with the following sequence: Hilyte-Fluor™488-ESARLQSGLRKAK-QXL520™-NH$_2$, producing final concentrations of 100 nM and 100 µM for the 3CL$^{pro}$ enzyme and UIVT3 substrate, respectively. The fluorescence intensity of the reaction was then measured over time as relative fluorescence units (RFU$_t$) for a period of 10 minutes, using an excitation wavelength of 485 and bandwidth of 20 nm and monitoring emission at 528 and bandwidth of 20 nm using a BioTek Synergy H1 multimode microplate reader.

The inhibition of each 3CL$^{pro}$ by inhibitor compounds was monitored by following the change in RFUs over time, using the initial slope of the progress curve to determine the initial rate (V$_i$). The percent inhibition of the 3CL$^{pro}$ enzymes was determined using the following equation:

$$\% \text{ Inhibition} = \left[1 - \frac{\text{Inhibited } 3CLpro \ RFU/s - \text{Background } RFU/s}{\text{Uninhibited } 3CLpro \ RFU/s - \text{Background } RFU/s}\right] * 100$$

Full IC$_{50}$ data were acquired for the compounds that showed greater than 50% inhibition of each 3CL$^{pro}$ at 100 µM of inhibitor compound. The IC$_{50}$ values were determined at ambient temperature from 100 µL assays performed in triplicate in the following buffer: 50 mM HEPES, 0.1 mg/mL BSA, 0.01% TritonX-100, 1 mM DTT. Kinetic assays were carried out in Costar 3694 EIA/RIA 96-Well Half Area, Flat Bottom, Black Polystyrene plates from Corning Incorporated. Each inhibitor was tested at concentrations of 0.313, 0.652, 1.25, 2.5, 5.0, 10.0, 20.0, 40.0, 60.0, 80.0, 100.0, and 120.0 µM; 1 µL of 100× inhibitor stock in DMSO was added to 79 µL of enzyme in assay buffer and the enzyme-inhibitor mixture was incubated for 10 minutes. The reaction was initiated by the addition of 20 µL of 10 µM UIVT3 substrate, producing final concentrations of 100 nM and 2 µM for the 3CL$^{pro}$ enzyme and UIVT3 substrate, respectively. The fluorescence intensity of the reaction was then measured over time as RFU$_t$ for a period of 20 minutes, using an excitation wavelength of 485 and bandwidth of 20 nm and monitoring emission at 528 and bandwidth of 20 nm using a BioTek Synergy H1 multimode microplate reader.

The percent inhibition of the 3CL$^{pro}$ enzymes was then plotted as a function of inhibitor concentration. The Sigma-Plot Enzyme Kinetics Wizard was used to fit the triplicate percent inhibition data and associated standard error to a non-linear Michaelis-Menten type regression model and determine the IC$_{50}$ for each enzyme using the following equation:

$$\% \text{ Inhibition} = \frac{\% I_{max} * [\text{Inhibitor}]}{IC_{50} + [\text{Inhibitor}]}$$

where % I$_{max}$ is the percent maximum inhibition of 3CL$^{pro}$ and the error in IC$_{50}$ values was determined as the error in the fitted parameter.

Crystallization and X-Ray Structure Determination of PEDV-, SARS-, and HKU4-3CLpro in Complex with Inhibitors The PEDV-3CL$^{pro}$:77 inhibitor complex was co-crystallized using the hanging-drop, vapor-diffusion method by setting up drops and adding 1 µL of purified PEDV-3CL$^{pro}$ (2.4 mg/mL), that had been incubated for three hours with a 3 molar excess of the compound 77, and 1 µL of reservoir solution: 0.20 M MIB pH 4.0 and 25% PEG-3350. Protein crystals appeared between 24 hours and 7 days after setting up crystallization plates. Crystals were harvested with a nylon loop, which was then swiped through the same mother-liquor solution supplemented with 15% MPD. The crystals were flash-cooled by plunging into liquid nitrogen and stored in shipping dewars containing liquid nitrogen until X-ray data collection at an available synchrotron could be performed.

The SARS-3CLpro:47 and SARS-3CLpro:77 inhibitor complexes were co-crystallized using the hanging-drop, vapor-diffusion method by setting up drops and adding 1 µL of purified SARS-3CL$^{pro}$ (10 mg/mL), that had been incubated for three hours with a 3 molar excess of the of compound 47 or 77, and 2 µL of reservoir solution: 3 mM DTT, 50 mM MES pH 6.0, 40 mM KCl, 1% MPD, and 5% PEG-10K. Protein crystallization plates were set up at 4° C. and protein crystals appeared 24 hours after setting up crystallization plates. Crystals were harvested with a nylon loop, which was then swiped through the same mother-liquor solution supplemented with 15% MPD. The crystals were cooled by plunging into liquid nitrogen and stored in shipping dewars containing liquid nitrogen until X-ray data collection at an available synchrotron could be performed.

The HKU4 3CL$^{pro}$-inhibitor complexes were co-crystallized from four different crystallization solutions. Briefly, the hanging-drop, vapor-diffusion method was used for crystallization by setting up drops and adding 1 µL of purified HKU4-CoV 3CL$^{pro}$ (2.5 mg/mL, 75 µM), that had been incubated for three hours with a 3 molar excess of the appropriate inhibitor, and 1 µL of reservoir solution. For compound 6: 17% PEG-3350, 0.1 M Bis Tris pH 5.5, 0.2 M NH$_4$OAc; for compound 27: 21% PEG-3350, 0.1 M ammonium acetate, 0.1 M Bis-Tris pH 5.5; for compound 64: 22% PEG-3350, 0.08 M NH$_4$OAc, 0.1 M Bis-Tris pH 5.5; for compound 67: 19% PEG-3350, 0.1 M Bis Tris pH 5.5, 01 M NH$_4$OAc. Protein crystals appeared between 7 and 14 days after setting up crystallization plates. Crystals were harvested with a nylon loop, which was then swiped through the same mother-liquor solution supplemented with 15% MPD. The crystals were cooled by plunging into liquid nitrogen and stored in shipping dewars containing liquid nitrogen until X-ray data collection at an available synchrotron could be performed.

The diffraction data for PEDV-3CL$^{pro}$:77, SARS-3CL$^{pro}$:47, SARS-3CL$^{pro}$:77, HKU4-3CL$^{pro}$:6, HKU4-3CL$^{pro}$:27, and HKU4-3CL$^{pro}$:67 were collected at 100 K at the Life Sciences Collaborative Access Team (LS-CAT) at the Advanced Photon Source (APS) at Argonne National Laboratories. Crystals were transferred from shipping dewars into automated dewars and then and mounted robotically on a goniostat while under a stream of N$_2$. X-ray data sets of 3CL$^{pro}$-inhibitor complexes were collected on a Rayonix 225 HE detector at a wavelength of 0.98 Å. The diffraction data for HKU4-3CLpro:64 was collected at 100K at an X-ray wavelength of 1.55 Å and a distance of 200 mm from the Raxis 4++ detector. X-ray data were processed and scaled using the program HLK2000 (Minor, et al., *Acta Phys Pol A* 2002, 101(5):613-619).

Those skilled in the art will recognize that numerous modifications can be made to the specific implementations described above. The implementations should not be limited to the particular limitations described. Other implementations may be possible.

While the inventions have been illustrated and described in detail in the drawings and foregoing description, the same is to be considered as illustrative and not restrictive in character, it being understood that only certain embodiments have been shown and described and that all changes and modifications that come within the spirit of the invention are desired to be protected.

It is intended that that the scope of the present methods and compositions be defined by the following claims. However, it must be understood that this disclosure may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims.

What is claimed is:

1. A compound of formula (I)

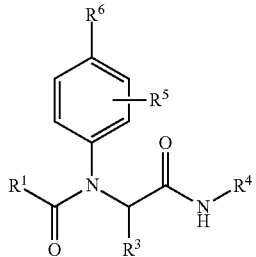

(I)

or a pharmaceutically acceptable salt or hydrate thereof, wherein:
$R^1$ is 1H-imidazole-4-yl;
$R^3$ is an alkyl, alkenyl, cycloalkyl, cycloalkenyl, heterocycle, aryl, or heteroaryl, each of which is optionally substituted;
$R^4$ is an alkyl, alkenyl, cycloalkyl, cycloalkenyl, heterocycle, aryl, or heteroaryl, each of which is optionally substituted, and $R^4$ is not t-butyl;
$R^5$ represents 1~4 substituents each of which is independently hydrogen, halo, or an alkyl, alkoxy, acyl, alkyl amide, cycloalkyl, cycloalkenyl, cycloalkyl amide, or aryl, each of which is optionally substituted; or $R^5$ represents 2-4 substituents where 2 adjacent substituents are taken together with the attached carbons to form an optionally substituted cyclic or heterocyclic moiety, and where any remaining substituents are each independently selected from the group as defined above; and
$R^6$ is halo or an alkyl amide, cycloalkyl amide, alkyl, alkenyl, alkoxy, acyl, cycloalkyl, cycloalkenyl, heterocycle, aryl, or heteroaryl, each of which is optionally substituted.

2. The compound of claim 1, wherein $R^3$ is an aryl or heterocycle, each of which is optionally substituted.

3. The compound of claim 2, wherein $R^3$ is thiophene-3-yl or pyridin-3-yl.

4. The compound of claim 1, wherein $R^4$ is an alkyl, cycloalkyl, or aryl, each of which is optionally substituted, but $R^4$ is not t-butyl.

5. The compound of claim 4, wherein $R^4$ is cyclohexyl, cyclopentyl, isobutyl, neopentyl, 3'-pyridylmethyl, or benzyl.

6. The compound of claim 1, wherein $R^5$ is hydrogen.

7. The compound of claim 1, wherein $R^6$ is an alkyl, alkylamide, cycloalkyl, or cycloalkylamide, each of which is optionally substituted.

8. The compound of claim 7, wherein $R^6$ is isobutyramide or t-butyl.

9. The compound of claim 1, wherein $R^5$ is hydrogen and $R^6$ is isobutyramide or t-butyl.

10. The compound of claim 1, wherein $R^3$ is pyridin-3-yl; $R^5$ is hydrogen; and $R^6$ is isobutyramide or t-butyl.

11. The compound of claim 1, wherein $R^3$ is pyridin-3-yl; $R^5$ is hydrogen; $R^6$ is t-butyl; and $R^4$ is selected from the group consisting of cyclohexyl, cyclopentyl, isobutyl, neopentyl, and benzyl.

12. The compound of claim 1, wherein $R^1$ is 1H-imidazole-4-yl; $R^3$ is pyridyl pyridin-3-yl; $R^5$ is hydrogen; and $R^4$ is selected from the group consisting of cyclohexyl, cyclopentyl, isobutyl, neopentyl, and benzyl.

13. The compound of claim 1, wherein $R^1$ is 1H-imidazole-4-yl; $R^3$ is pyridin-3-yl; $R^5$ is hydrogen; $R^6$ is t-butyl; and $R^4$ is selected from the group consisting of cyclohexyl, cyclopentyl, isobutyl, neopentyl, and benzyl.

14. The compound of claim 1, wherein the compound has the following structure of

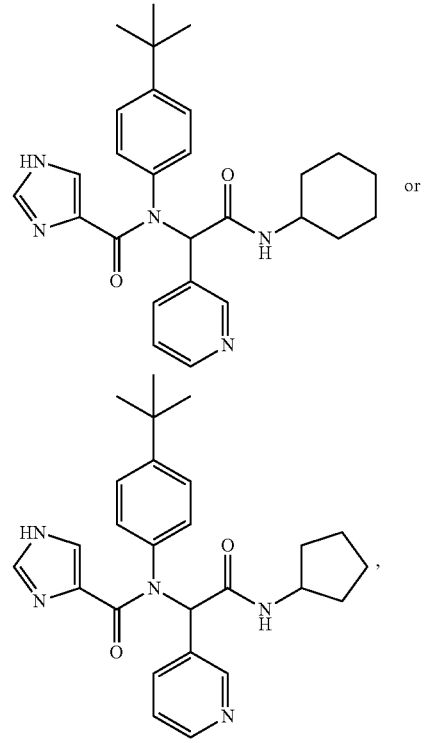

or a pharmaceutically acceptable salt thereof.

15. A pharmaceutical composition comprising a compound of claim 1, or a pharmaceutically acceptable salt thereof, together with one or more pharmaceutically acceptable carriers, diluents, and excipients.

16. A method for treating a patient with a viral infection, the method comprising the step of administering a therapeutically effective amount of a compound of claim 1, together with one or more pharmaceutically acceptable carriers, diluents, and excipients, to the patient in need of relief from said viral infection.

17. A method for treating a patient with a viral infection, the method comprising the step of administering a therapeutically effective amount of a compound of claim 1, in combination with one or more therapeutically effective compounds, to the patient in need of relief from said viral infection.

18. A method for treating a patient with a viral infection, the method comprising the step of administering a therapeutically effective amount of a compound of formula (I):

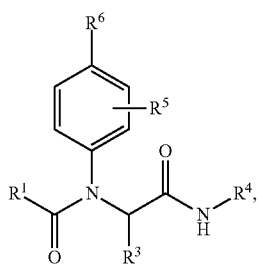

or a pharmaceutically acceptable salt or hydrate thereof, wherein:

$R^1$ is 1H-imidazole-4-yl;

$R^3$ is an alkyl, alkenyl, cycloalkyl, cycloalkenyl, heterocycle, aryl, or heteroaryl, each of which is optionally substituted;

$R^4$ is an alkyl, alkenyl, cycloalkyl, cycloalkenyl, heterocycle, aryl, or heteroaryl, each of which is optionally substituted, and $R^4$ is not t-butyl;

$R^5$ represents 1~4 substituents each of which is independently hydrogen, halo, or an alkyl, alkoxy, acyl, alkyl amide, cycloalkyl, cycloalkenyl, cycloalkyl amide, or aryl, each of which is optionally substituted; or $R^5$ represents 2-4 substituents where 2 adjacent substituents are taken together with the attached carbons to form an optionally substituted cyclic or heterocyclic moiety, and where any remaining substituents are each independently selected from the group as defined above; and $R^6$ is halo or an alkyl amide, cycloalkyl amide, alkyl, alkenyl, alkoxy, acyl, cycloalkyl, cycloalkenyl, heterocycle, aryl, or heteroaryl, each of which is optionally substituted.

* * * * *